United States Patent
Yaginuma et al.

(10) Patent No.: US 11,466,249 B2
(45) Date of Patent: Oct. 11, 2022

(54) CELL TISSUE PRODUCING METHOD AND APPARATUS, AND NON-TRANSITORY RECORDING MEDIUM STORING CELL TISSUE PRODUCING PROGRAM

(71) Applicant: RICOH COMPANY, LTD., Tokyo (JP)

(72) Inventors: Hidekazu Yaginuma, Kanagawa (JP); Naoki Satoh, Kanagawa (JP); Tomoyuki Aratani, Kanagawa (JP); Chihiro Kubo, Kanagawa (JP); Daisuke Takagi, Kanagawa (JP); Momoko Shionoiri, Kanagawa (JP); Natsuko Iwashita, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 465 days.

(21) Appl. No.: 16/299,873

(22) Filed: Mar. 12, 2019

(65) Prior Publication Data
US 2019/0284524 A1    Sep. 19, 2019

(30) Foreign Application Priority Data

Mar. 16, 2018 (JP) .............................. JP2018-049753
Dec. 13, 2018 (JP) .............................. JP2018-233031

(51) Int. Cl.
| | | |
|---|---|---|
| *C12N 5/00* | (2006.01) | |
| *G16B 40/00* | (2019.01) | |
| *B33Y 10/00* | (2015.01) | |
| *C12M 1/26* | (2006.01) | |
| *G16B 5/00* | (2019.01) | |

(52) U.S. Cl.
CPC ............ *C12N 5/0068* (2013.01); *B33Y 10/00* (2014.12); *C12M 33/00* (2013.01); *G16B 40/00* (2019.02); *C12N 2533/90* (2013.01); *G16B 5/00* (2019.02)

(58) Field of Classification Search
None
See application file for complete search history.

(56) References Cited

U.S. PATENT DOCUMENTS

| | | |
|---|---|---|
| 2005/0279730 A1 | 12/2005 | Miyake et al. |
| 2007/0218554 A1 | 9/2007 | Miyake et al. |
| 2007/0243613 A1* | 10/2007 | Miyake ............... B01L 3/5085 435/395 |
| 2010/0330665 A1 | 12/2010 | Miyake et al. |
| 2011/0143439 A1 | 6/2011 | Miyake et al. |
| 2016/0175834 A1 | 6/2016 | Seo et al. |
| 2016/0288414 A1 | 10/2016 | Ozbolat et al. |
| 2017/0267975 A1 | 9/2017 | Hasegawa et al. |

FOREIGN PATENT DOCUMENTS

| | | |
|---|---|---|
| JP | 2002-355026 | 12/2002 |
| JP | 2005-261432 | 9/2005 |
| JP | 41 48500 | 7/2008 |
| JP | 4699361 | 3/2011 |
| JP | 4711164 | 4/2011 |
| JP | 4761731 | 6/2011 |
| JP | 4797396 | 8/2011 |
| JP | 5077449 | 9/2012 |
| JP | 5164156 | 12/2012 |
| JP | 5477423 | 2/2014 |
| JP | 2015-177755 | 10/2015 |
| JP | 2016-116489 | 6/2016 |
| JP | 2017-163931 | 9/2017 |
| JP | 2017-169560 | 9/2017 |
| JP | 2019-017255 | 2/2019 |
| WO | 2014/112633 | 7/2014 |
| WO | WO 2018/026172 A1 | 2/2018 |

OTHER PUBLICATIONS

Extended European Search Report dated Jun. 25, 2019 in European Patent Application No. 19161590.5 citing documents AA-AE therein, 8 pages.

European Office Action dated Sep. 24, 2020 in European Patent Application No. 19161590.5, citing documents AO and AX therein, 6 pages.

Jia, J., et al., "Engineering alginate as bioink for bioprinting", Acta Biomaterialia, vol. 10, No. 10, Jul. 1, 2014 (Jul. 1, 2014), pp. 4323-4331, XP055447357, Amsterdam, NL ISSN: 1742-7061, DOI: 10.1016/j.actbio.2014.06.034.

Japanese Office Action dated Jul. 12, 2022, in Japanese Application No. 2018-233031, with English translation, 6 pages.

* cited by examiner

*Primary Examiner* — Nghi V Nguyen
(74) *Attorney, Agent, or Firm* — Grüneberg and Myers PLLC

(57) ABSTRACT

Provided is a cell tissue producing method including: a cell adhesive portion forming step of forming a cell adhesive portion formed of a cell adhesive material and having a predetermined shape at a predetermined position over a substrate having a cell non-adhesive surface; and a cell locating step of discharging a cell suspension containing at least cells and a cell drying inhibitor onto the cell adhesive portion in the form of a liquid droplet to locate the cells.

9 Claims, 19 Drawing Sheets

CELL TISSUE PRODUCING METHOD AND APPARATUS, AND NON-TRANSITORY RECORDING MEDIUM STORING CELL TISSUE PRODUCING PROGRAM

CROSS-REFERENCE TO RELATED APPLICATIONS

The present application claims priority under 35 U.S.C. § 119 to Japanese Patent Application No. 2018-049753 filed Mar. 16, 2018 and Japanese Patent Application No. 2018-233031 filed Dec. 13, 2018. The contents of which are incorporated herein by reference in their entirety.

BACKGROUND OF THE INVENTION

Field of the Invention

The present disclosure relates to a cell tissue producing method and apparatus, and a non-transitory recording medium storing a cell tissue producing program.

Description of the Related Art

In recent years, along with the evolution of the stem cell technologies, techniques for artificially forming tissues using cells have been being developed.

In artificial formation of tissues, a technique for locating cells in an optional manner is indispensable. Hence, various attempts are made, and, for example, cell sheet methods, spheroid lamination methods, gel extrusion methods, and inkjet methods are known.

Meanwhile, attempts are also made to improve the very substrates over which cells are to be located For example, there is proposed a three-dimensional culture structure producing method of forming a layer of a cell support material precursor aqueous solution containing biocompatible particles and a cell support material precursor over a substrate, applying a cell support material precursor gelation aqueous solution that in response to contacting the cell support material precursor aqueous solution, causes the cell support material precursor to undergo gelation over the layer of the cell support material precursor aqueous solution, and then applying a cell layer forming material containing cells over the layer of the cell support material, to make the cells adhere to the cell support material (for example, see Unexamined Japanese Patent Application Publication No. 2017-169560). This proposal describes that a gelatinous polysaccharide may be contained in the cell support material.

SUMMARY OF THE INVENTION

According to one aspect of the present disclosure, a cell tissue producing method of the present disclosure includes a cell adhesive portion forming step of forming a cell adhesive portion formed of a cell adhesive material and having a predetermined shape at a predetermined position over a substrate having a cell non-adhesive surface, and a cell locating step of discharging a cell suspension containing at least cells and a cell drying inhibitor onto the cell adhesive portion in the form of a liquid droplet to locate the cells.

DESCRIPTION OF THE EMBODIMENTS

Figure 1:
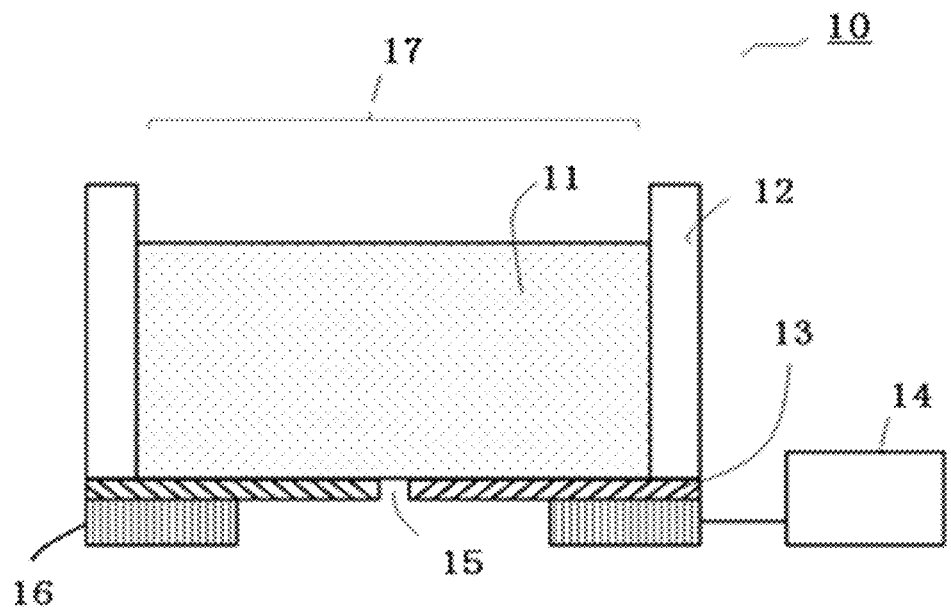
FIG. 1 is a schematic view illustrating an example of an inkjet head used for discharging a liquid droplet.

Techniques for locating cells over substrates by inkjet methods are effective for artificially forming cell tissues, because the techniques, which can locate the cells in a state of being suspended in a liquid, can suppress damage to the cells and provide easy controllability of the number of cells to be discharged.

However, there are many problems before stably discharging a cell suspension (also referred to as cell ink) suspending cells by inkjet methods. For example, most ink materials commonly used in image formation by inkjet methods cannot be used in cell inks because these ink materials are highly damaging to cells. Further, there is a need for discharging a cell ink at a dispersion concentration lower than the concentration of, for example, pigments in inks that have been used in existing image formation. Furthermore, because drying of liquid droplets of a cell ink after cells have landed over a substrate induces cell death, quick-drying ink blending methods used in existing image formation cannot be applied as is. Moreover, because there is a need for locating a cell ink in a manner that liquid droplets do not merge with each other, cells cannot be located over a substrate at a high density.

Further, Unexamined Japanese Patent Application Publication No. 2017-169560 does not describe positioning (pattern arrangement) of biocompatible particles.

As a result of persistent studies, the present inventors have found that a cell tissue producing method having the following configuration is effective as a cell tissue producing method capable of producing a cell tissue having a cell pattern in which a desired number of cells are located per predetermined position over a substrate.

The cell tissue producing method of the present disclosure can form a cell pattern in a short time, improve the shape accuracy of the pattern shape, improve the accuracy of locating a desired number of cells, and increase the survival rate of the located cells.

Furthermore, the cell tissue producing method of the present disclosure can form a cell pattern using a plurality of cells and artificially form a cell tissue formed of a plurality of cells.

(Cell Tissue Producing Method and Apparatus and Non-Transitory Recording Medium Storing Cell Tissue Producing Program)

A cell tissue producing method of the present disclosure includes a cell adhesive portion forming step of forming a cell adhesive portion formed of a cell adhesive material and having a predetermined shape at a predetermined position over a substrate having a cell non-adhesive surface.

The cell tissue producing method of the present disclosure includes a cell adhesive portion forming step of forming a cell non-adhesive portion formed of a cell non-adhesive material and having a predetermined shape at a predetermined position over a substrate having a cell adhesive surface, to form a cell adhesive portion, which is an exposed portion of the cell adhesive surface.

The cell tissue producing method of the present disclosure includes a cell locating step of discharging a cell suspension containing at least cells and a cell drying inhibitor onto the cell adhesive portion in the form of a liquid droplet to locate the cells.

The cell tissue producing method of the present disclosure may include other steps as needed.

A cell tissue producing apparatus of the present disclosure includes a cell adhesive portion forming unit configured to form a cell adhesive portion formed of a cell adhesive material and having a predetermined shape at a predetermined position over a substrate having a cell non-adhesive surface.

The cell tissue producing apparatus of the present disclosure includes a cell adhesive portion forming unit configured to form a cell non-adhesive portion formed of a cell non-adhesive material and having a predetermined shape at a predetermined position over a substrate having a cell adhesive surface, to form a cell adhesive portion, which is an exposed portion of the cell adhesive surface.

The cell tissue producing apparatus of the present disclosure includes a cell locating unit configured to discharge a cell suspension containing at least cells and a cell drying inhibitor onto the cell adhesive portion in the form of a liquid droplet to locate the cells.

The cell tissue producing apparatus of the present disclosure may include other units as needed.

A non-transitory recording medium storing a cell tissue producing program of the present disclosure stores a cell tissue producing program for causing a computer to execute a process including forming a cell adhesive portion formed of a cell adhesive material and having a predetermined shape at a predetermined position over a substrate having a cell non-adhesive surface.

The non-transitory recording medium storing a cell tissue producing program of the present disclosure stores a cell tissue producing program for causing a computer to execute a process including forming a cell non-adhesive portion formed of a cell non-adhesive material and having a predetermined shape at a predetermined position over a substrate having a cell adhesive surface, to form a cell adhesive portion, which is an exposed portion of the cell adhesive surface.

The non-transitory recording medium storing a cell tissue producing program of the present disclosure stores a cell tissue producing program for causing a computer to execute a process including discharging a cell suspension containing at least cells and a cell drying inhibitor onto the cell adhesive portion in the form of a liquid droplet to locate the cells.

The cell tissue producing apparatus of the present disclosure is the same as carrying out the cell tissue producing method of the present disclosure. Hence, the details of the producing apparatus of the present disclosure will be specified through description of the producing method of the present disclosure, or the details of the producing method of the present disclosure will be specified through description of the producing apparatus of the present disclosure. The non-transitory recording medium storing the cell tissue producing program of the present disclosure realizes the cell tissue producing method of the present disclosure with the use of, for example, computers as hardware resources. Hence, the details of the non-transitory recording medium storing the cell tissue producing program of the present disclosure will also be specified through description of the producing method of the present disclosure.

The present disclosure has an object to provide a cell tissue producing method for producing a cell tissue that has a high survival rate of located cells.

The present disclosure can provide a cell tissue producing method for producing a cell tissue that has a high survival rate of located cells.

<Cell Adhesive Portion Forming Step and Unit>

The cell adhesive portion forming step is a step of forming a cell adhesive portion formed of a cell adhesive material and having a predetermined shape at a predetermined position over a substrate having a cell non-adhesive surface.

In the cell adhesive portion forming step, a cell adhesive portion having a predetermined shape is formed at a predetermined position over a substrate. In the present disclosure, formation of a cell adhesive portion having a predetermined shape at a predetermined position will also be referred to as formation of a cell adhesive portion in a pattern. The conditions such as the position and shape of a cell adhesive portion can be arbitrarily set by a worker or a user. Cell adhesive portions are formed over a substrate according to the size of and the interval between cell adhesive portions set by the worker or the user.

The method for forming cell adhesive portions in the pattern over a substrate having a cell non-adhesive surface is not particularly limited and may be appropriately selected depending on the intended purpose. Examples of the method include the methods described below.

In one method, a cell non-adhesive surface is covered with a mask having the pattern, to form regions in which the cell non-adhesive surface is exposed and regions covered with the mask. Next, the cell adhesive material is coated over the entire region to form a layer of the cell adhesive material. Then, the mask is removed. As a result, there remains the layer formed of the cell adhesive material in the unmasked regions. In this way, cell adhesive portions in the pattern are formed (hereinafter, this method will also be referred to as forming method by a mask pattern).

In another method, liquid droplets of the cell adhesive material are discharged onto a substrate having a cell non-adhesive surface using an inkjet head, to form layers formed of the cell adhesive material. Here, cell adhesive portions in the pattern are formed with adjustment of the timing to discharge the liquid droplets and the discharging amount of the liquid droplets (hereinafter, this method will also be referred to as forming method by inkjet).

As the inkjet head used to discharge liquid droplets of the cell adhesive material, the same inkjet head as an inkjet head used to discharge liquid droplets of a cell suspension (cell ink) described below can be used. Hence, the inkjet head will be described in detail in the section <<Inkjet head for discharging liquid droplets>> below.

A specific embodiment of the step of forming cell adhesive portions in the pattern shape will be described in detail below.

<<Substrate Having Cell Non-Adhesive Surface>>

The substrate is not particularly limited so long as the substrate has a cell non-adhesive surface over a surface. It is more preferable that the cell adhesive material be able to adsorb to the substrate easily.

Cell non-adhesiveness refers to a lower adhesiveness with intended cells than at least the adhesiveness of the cell adhesive material to be used.

Examples of the material of the substrate having the cell non-adhesive surface include the organic materials and the inorganic materials presented below. One of these materials may be used alone or two or more of these materials may be used in combination.

The organic materials are not particularly limited and may be appropriately selected depending on the intended purpose. Examples of the organic materials include polyethylene terephthalate (PET), polystyrene (PS), polycarbonate (PC), TAC (triacetyl cellulose), polyimide (PI), nylon (Ny), low density polyethylene (LDPE), medium density polyethylene (MDPE), vinyl chloride, vinylidene chloride, polyphenylene sulfide, polyether sulfone, polyethylene naphthalate, polypropylene, acrylic-based materials such as urethane acrylate, cellulose, silicone-based materials such as polydimethyl siloxane (PDMS), polyvinyl alcohol (PVA), metal alginates such as calcium alginate, polyacrylamide, methyl cellulose, and gelatinous materials such as agarose.

The inorganic materials are not particularly limited and may be appropriately selected depending on the intended purpose. Examples of the inorganic materials include glass and ceramics.

The substrate having the cell non-adhesive surface can also be obtained by coating a material having cell non-adhesiveness over an arbitrary substrate.

Examples of the preferable embodiment of the substrate having the cell non-adhesive surface include a substrate provided with, for example, a polydimethyl siloxane (PDMS) layer, a gel layer formed of a metal alginate (e.g., calcium alginate), a polyhydroxyethyl methacrylate (pHEMA) layer, or a polyethylene glycol (PEG) layer over a surface.

<<Cell Adhesive Material>>

Examples of the cell adhesive material include a protein selected from the extracellular matrix.

The protein selected from the extracellular matrix is not particularly limited and may be appropriately selected depending on the intended purpose. Examples of the protein include collagen, laminin, fibronectin, elastin, fibrin, and matrigel. One of these proteins may be used alone or two or more of these proteins may be used in combination.

As the cell adhesive material, particles having cell adhesiveness described below can also be used.

The particles having cell adhesiveness are not particularly limited and may be appropriately selected depending on the intended purpose so long as the particles having cell adhesiveness have affinity with living things such as cells. Examples of the particles having cell adhesiveness include gelatin particles and collagen particles. One of these kinds of particles may be used alone or two or more of these kinds of particles may be used in combination.

Gelatin particles having a particulate shape can improve adhesiveness of cells with the substrate, and can be present in a cell tissue without being degraded by the cells for a longer time than gelatin having a non-particulate shape. Therefore, there are advantages that the gelatin particles having a particulate shape can improve adhesiveness of cells and are used as a source of nutrients for the cells for a long term.

For example, the shape of the particles having cell adhesiveness is not particularly limited and may be appropriately selected depending on the intended purpose.

Examples of the shape of the particles having cell adhesiveness include a spherical shape, a linear shape, a mesh-patterned shape, and an irregular shape. One of these shapes may be used alone or two or more of these shapes may be used in combination.

The cumulant diameter of the particles having cell adhesiveness is not particularly limited, may be appropriately selected depending on the intended purpose, and is preferably 0.1 micrometers or greater but 1.0 micrometer or less and more preferably 0.30 micrometers or greater but 0.70 micrometers or less. The cumulant particle diameter can be measured with a concentrate particle diameter analyzer (product name: FPAR-1000, available from Otsuka Electronics Co., Ltd.), using a sample liquid obtained in Sample liquid preparation example described below, under the measurement conditions described below.

Sample Liquid Preparation Example

The particles having cell adhesiveness are dispersed in pure water obtained with a pure water producing apparatus (product name: GSH-2000, available from ADVANTEC Co., Ltd.), at a concentration of 0.5% by mass. The liquid amount for measurement is 5 mL. The particles are subjected to dispersion treatment using a stirrer for a 20 mm rotor, with stirring kept for about one day at 200 rpm. In this way, the sample liquid can be prepared.

—Measurement Conditions—

Solvent: water (refractive index: 1.3314, viscosity at 25 degrees C.: 0.884 mPa-s (cP), with appropriate setting of the optimum light volume adjustment by an ND filter)

Measuring probe: a probe for a concentrated system

Measurement routine: measurement at 25 degrees C. for 180 seconds, then measurement at 25 degrees C. for 600 seconds (monitoring of the change of the particle diameter during gradual change of the liquid temperature from 25 degrees C. to 35 degrees C. started in response to temperature change to 35 degrees C. on the main body side), and then measurement at 35 degrees C. for 180 seconds When the particles having cell adhesiveness are gelatin particles, gelatin serving as the material of the gelatin particles is not particularly limited and may be appropriately selected depending on the intended purpose. Examples of the gelatin include product name: APH-250 (available from Nitta Gelatin Inc.).

It is preferable that the particles having cell adhesiveness be cross-linked by a cross-linking agent in the structure. By cross-linking by a cross-linking agent, the cumulant diameter of the particles having cell adhesiveness can be made small and cell proliferation can be promoted over the cell tissue containing the particles having cell adhesiveness.

The cross-linking agent is not particularly limited and may be appropriately selected depending on the intended purpose. Examples of the cross-linking agent include: aldehydes such as glutaraldehyde and formaldehyde; glycidyl ethers such as ethylene propylene diglycidyl ether, glycerol polyglycidyl ether, diglycerol polyglycidyl ether, sorbitol polyglycidyl ether, and ethylene glycol diglycidyl ether; isocyanates such as hexamethylene diisocyanate, α-tolidine isocyanate, tolylene diisocyanate, naphthylene-1,5-diisocyanate, 4,4-diphenylmethane diisocyanate, and triphenylmethane-4,4,4-triisocyanate; calcium gluconate; methyl (1S, 2R,6S)-2-hydroxy-9-(hydroxymethyl)-3-oxabicyclo [4.3.0] nona-4,8-diene-5-carboxylate (genipin); combination of polyphenol and an oxidant such as horseradish peroxidase; and a compound containing a succinimide group. One of these cross-linking agents may be used alone or two or more of these cross-linking agents may be used in combination. Among these cross-linking agents, aldehydes are preferable and glutaraldehyde is more preferable.

The content of the cross-linking agent is preferably 1% by mass or greater but 20% by mass or less and more preferably 2% by mass or greater but 10% by mass or less relative to the total amount of the material of the particles having cell adhesiveness. When the content of the cross-linking agent is 1% by mass or greater but 20% by mass or less, the cumulant diameter of the particles having cell adhesiveness can be made small and cell proliferation can be promoted over the cell tissue containing the particles having cell adhesiveness.

The content of the particles having cell adhesiveness is preferably 0.5% by mass or greater but 10% by mass or less and more preferably 1% by mass or greater but 5% by mass or less relative to the total amount of the solution of the material containing the particles having cell adhesiveness. When the content of the particles having cell adhesiveness 0.5% by mass or greater but 10% by mass or less, cell proliferation can be promoted, with sufficient adhesion of cells with the cell tissue, which is a three-dimensional cell assembly.

—Method for Producing Particles Having Cell Adhesiveness—

The particles having cell adhesiveness can be produced in the manner described below, using gelatin as a material, for example.

As the particles having cell adhesiveness, gelatin is mixed with water at a concentration of 2% by mass, and dissolved in the water in a hot water bath of 60 degrees C., to obtain a 2% by mass gelatin aqueous solution. Next, the 2% by mass gelatin aqueous solution heated to 40 degrees C. is poured in an amount of 40 mL into a 200 mL beaker and stirred. Subsequently, acetone (60 g) is added in a lump to the resultant, to obtain a white turbid liquid (coacervation).

An aqueous solution of 24% by mass or greater but 26% by mass or less of glutaraldehyde as a cross-linking agent is added in an amount of, for example, 160 microliters (i.e., a glutaraldehyde content of 5% by mass relative to the total amount of gelatin) to the white turbid liquid, and the resultant is retained in a hot water bath of 60 degrees C. for 30 minutes under stirring at about 300 rpm. Gradually, the white turbid liquid turns to a creamy color. In this way, gelatin particles can be formed.

Next, the resultant is returned to room temperature (25 degrees C.), and acetone (100 g) is added to the resultant, to make the gelatin particles undergo coagulation sedimentation to obtain a precipitate.

Supernatant removal and acetone washing are repeated a several times, and water and the unreacted portion of the cross-linking agent are removed from the obtained precipitate, followed by filtration as needed. Subsequently, the precipitate is dried on a hot plate at 60 degrees C., and dried on the hot plate at 50 degrees C. at a reduced pressure for 1 hour, to obtain a powder of gelatin particles (particles having cell adhesiveness).

In addition to the foregoing, with changes of the "cell adhesive material" to "cell non-adhesive material" and the "substrate having a cell non-adhesive surface" to "substrate having a cell adhesive surface", the cell adhesive portion forming step may be a step of forming a cell non-adhesive portion formed of the cell non-adhesive material and having a predetermined shape at a predetermined position over the substrate having a cell adhesive surface, to form a cell adhesive portion, which is an exposed portion of the cell adhesive surface.

<<Substrate Having Cell Adhesive Surface>>

The substrate is not particularly limited so long as the substrate has a cell adhesive surface over a surface. It is more preferable that the cell non-adhesive material be able to adsorb to the substrate easily.

Cell adhesiveness refers to a higher adhesiveness with intended cells than at least the adhesiveness of the cell non-adhesive material to be used.

The substrate having the cell adhesive surface is not particularly limited so long as cells adhere to the substrate. Examples of the substrate having the cell adhesive surface include a culture dish or a bottom surface of a microplate commonly used for, for example, cell culture, and a substrate coated with an adhesive material in the cell adhesive material.

<<Cell Non-Adhesive Material>>

The cell non-adhesive material is not particularly limited and may be appropriately selected depending on the intended purpose. For example, the same material as the material having the cell non-adhesiveness described above can be used.

<Cell Locating Step and Unit>

The cell locating step is a step of discharging a cell suspension containing at least cells and a cell drying inhibitor onto the cell adhesive portion in the form of a liquid droplet to locate the cells.

By discharging liquid droplets of the cell suspension onto the cell adhesive portions in the pattern in the cell locating step, it is possible to seed cells onto the cell adhesive portions in the pattern and form a cell pattern.

The cell locating step, which is divided into a liquid droplet discharging step of discharging the cell suspension in the form of a liquid droplet and a step of discharging a liquid droplet onto a cell adhesive portion to locate the cells on the cell adhesive portion, will be described below step by step.

<<Liquid Droplet Discharging Step and Unit>>

The liquid droplet discharging step is a step of discharging a cell suspension (cell ink) containing at least cells and a cell drying inhibitor in the form of a liquid droplet.

As a unit configured to discharge a liquid droplet of the cell suspension (cell ink) containing the cells and the cell drying inhibitor onto a substrate, a liquid droplet discharging unit of an inkjet type is preferable.

Examples of the liquid droplet discharging unit of the inkjet type include a so-called piezo type (for example, see Japanese Examined Patent Publication No. 02-51734) using a piezoelectric element as a pressure generating unit to pressurize the cell suspension (cell ink) to change the volume of the cell suspension and discharge liquid droplets, a so-called thermal type (for example, see Japanese Examined Patent Publication No. 61-59911) using a heating resistor to heat the cell suspension and generate bubbles, and an electrostatic type (for example, see Japanese Unexamined Patent Application Publication No. 06-71882) using a vibration plate and an electrode disposed counter to the vibration plate to deform the vibration plate by an electrostatic force generated between the vibration plate and the electrode and change the volume of the cell suspension to discharge liquid droplets.

A specific embodiment of an inkjet head used for discharging the cell suspension (cell ink) containing the cells and the cell drying inhibitor in the form of a liquid droplet will be described below.

<<Inkjet Head for Discharging Liquid Droplets>>

FIG. 1 is a schematic view illustrating an example of an inkjet head used for discharging a liquid droplet.

In FIG. 1, a piezoelectric element is used as a pressure generating unit.

Figure 2A:
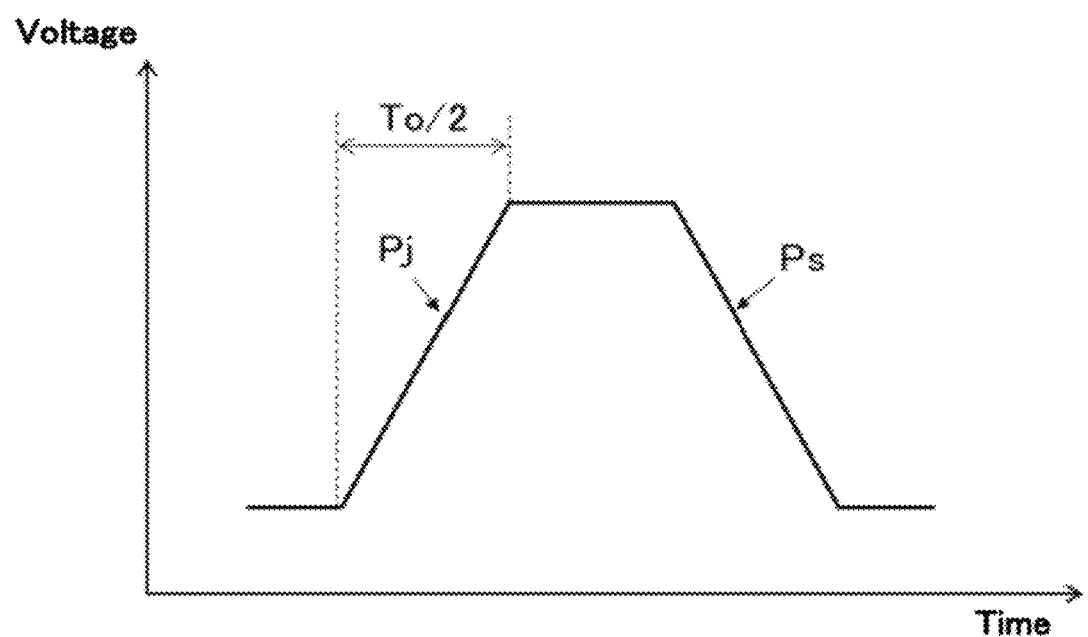
FIG. 2A is a schematic graph plotting an example of an input waveform to an inkjet head.
Figure 2B:
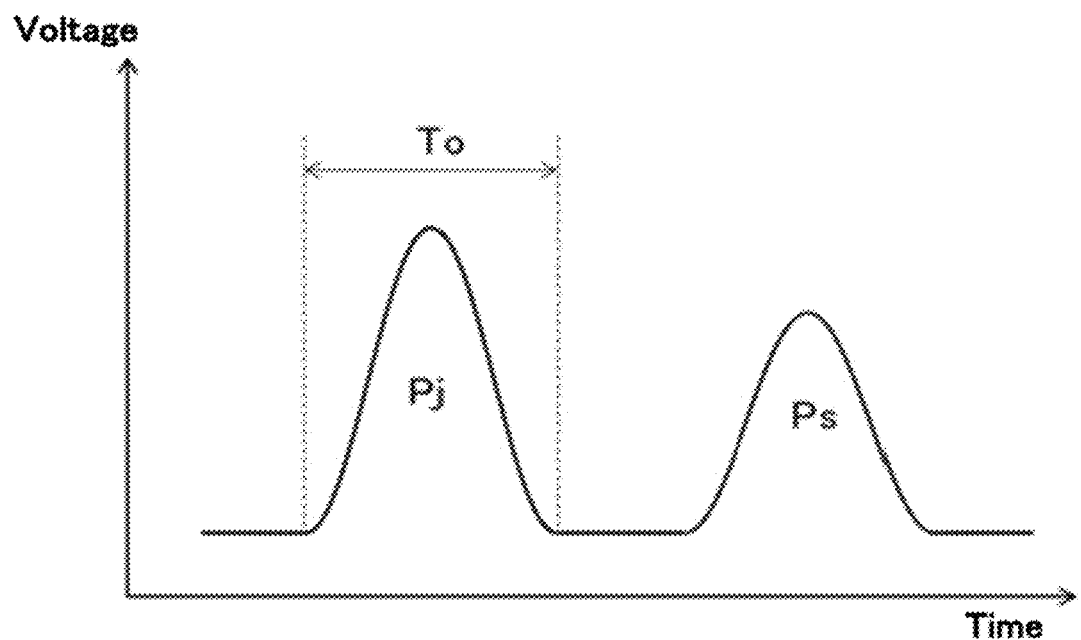
FIG. 2B is a schematic graph plotting an example of an input waveform to an inkjet head.

FIG. 2A and FIG. 2B are schematic graphs plotting examples of input waveforms to the inkjet head.

A liquid droplet discharging head 10 includes a liquid chamber 12 retaining a cell suspension 11, a nozzle 15, a membrane 13 as a membranous member, an exciting unit 16 configured to apply vibration to the membrane 13, and a driving unit 14 configured to apply a voltage to the exciting unit 16 as a specific driving signal in order to vibrate the exciting unit 16.

The liquid chamber 12 is provided with an atmospherically exposed portion 17 configured to expose the interior of the liquid chamber to the atmosphere.

The liquid droplet discharging head 10 is configured to discharge a liquid droplet of the cell suspension through the nozzle by applying vibration to the cell suspension.

The driving unit 14 is capable of applying a discharging waveform Pj to the exciting unit 16 as a driving signal, and by controlling the vibration state of the membrane 13, can cause the cell suspension 11 retained in the liquid chamber 12 to be discharged in the form of a liquid droplet. The discharging waveform Pj may be set as a driving signal that contains a natural vibration period To of the membrane 13 in order to cause the cell suspension 11 to be discharged at a lower voltage under resonant vibration of the membrane 13. As the discharging waveform Pj, not only a triangle wave and a sine wave, but also a triangle wave passed through a low pass filter to have gentle edges may be used. Further, the driving unit 14 is capable of applying a vibration damping waveform Ps for suppressing residual vibration of the membrane after a liquid droplet is discharged, to the exciting unit 16 as a driving signal. Hence, residual vibration of the membrane after a liquid droplet is formed is suppressed quickly, making it possible to perform continuous discharging at a higher frequency. Moreover, a satellite or a mist can be reduced, making it possible to perform more minute control of a liquid droplet amount. As the vibration damping waveform Ps, not only a triangle wave and a sine wave, but also a triangle wave passed through a low pass filter to have gentle edges may be used.

The amount of the cell suspension 11 retained in the liquid chamber 12 is not particularly limited. For example, a liquid may be retained in an amount of about from 1 microliter through 1 mL. Particularly, in the case of using an expensive liquid such as a cell suspension in which cells are dispersed, it is preferable that formation of liquid droplets can be performed with a small liquid amount, and it is preferable that a liquid amount of about from 1 microliter through 50 microliters can be retained.

The shape of the membrane 13 may be a circular shape, an elliptic shape, or a quadrangular shape.

The material of the membrane 13 is not particularly limited. If the material of the membrane is extremely flexible, the membrane easily undergoes vibration and is not easily able to stop vibration immediately when there is no need for discharging a liquid droplet. Therefore, a material having a certain degree of hardness is preferable. As the material of the membrane 13, for example, a metal material, a ceramic material, and a polymeric material having a certain degree of hardness can be used.

It is preferable that the nozzle 15 be formed in the center of the membrane 13 as a through hole having substantially a perfect circle shape.

Examples of the exciting unit 16 include a piezoelectric element. Application of a voltage to the piezoelectric element causes a compressive stress to be applied in the horizontal direction of the drawing sheet, making it possible for the membrane 13 to deform. As the material of the piezoelectric element, for example, lead zirconate titanate commonly used may be used. In addition, various piezoelectric materials may be used, such as bismuth iron oxide, metal niobate, barium titanate, or materials obtained by adding metals or different oxides to these materials.

The unit configured to apply vibration to the membrane 13 to deform the membrane 13 is not limited to a piezoelectric element. For example, a material having a different coefficient of linear expansion from the coefficient of linear expansion of the membrane 13 may be pasted over the membrane. By heating the material, it is possible to deform the membrane 13, utilizing the difference between the coefficients of linear expansion. Here, for example, a heater is formed in the material having the different coefficient of linear expansion, such that the membrane 13 can deform when the heater is heated in response to electrification.

Next, the cell suspension (cell ink) will be described.

The cell suspension (cell ink) contains at least cells and a cell drying inhibitor. Further, the cell suspension (cell ink) contains a dispersion medium in which cells are to be dispersed, and may further contain other additive materials such as a dispersant and a pH adjustor as needed.

<<<Cells>>>

For example, the kind of the cells is not particularly limited and may be appropriately selected depending on the intended purpose. Taxonomically all kinds of cells can be used regardless of whether the cells are eukaryotic cells, prokaryotic cells, multicellular organism cells, and unicellular organism cells. One of these kinds of cells may be used alone or two or more of these kinds of cells may be used in combination.

Examples of the eukaryotic cells include animal cells, insect cells, plant cells, and fungi. One of these kinds of eukaryotic cells may be used alone or two or more of these kinds of eukaryotic cells may be used in combination. Among these eukaryotic cells, animal cells are preferable. When a cell assembly is formed with the cells, adherent cells having cell adhesiveness of a level at which cells adhere with each other and are not isolated without a physicochemical treatment are more preferable.

Adherent cells are not particularly limited and may be appropriately selected depending on the intended purpose. Examples of adherent cells include differentiated cells and undifferentiated cells. One of these kinds of adherent cells may be used alone or two or more of these kinds of adherent cells may be used in combination.

Examples of differentiated cells include: hepatocytes, which are parenchymal cells of a liver; stellate cells; Kupffer cells; endothelial cells such as vascular endothelial cells, sinusoidal endothelial cells, and corneal endothelial cells; fibroblasts; osteoblasts; osteoclasts; periodontal ligament-derived cells; epidermal cells such as epidermal keratinocytes; epithelial cells such as tracheal epithelial cells, intestinal epithelial cells, cervical epithelial cells, and corneal epithelial cells; mammary glandular cells; pericytes; muscle cells such as smooth muscle cells and myocardial cells; renal cells; pancreatic islet cells; nerve cells such as peripheral nerve cells and optic nerve cells; chondrocytes; and bone cells. Adherent cells may be primary cells directly taken from tissues or organs, or may be cells obtained by passaging primary cells a few times. One of these kinds of cells may be used alone or two or more of these kinds of cells may be used in combination.

Undifferentiated cells are not particularly limited and may be appropriately selected depending on the intended purpose. Examples of undifferentiated cells include: pluripotent stem cells such as embryotic stem cells, which are undifferentiated cells, and mesenchymal stem cells having pluripotency; unipotent stem cells such as vascular endothelial progenitor cells having unipotency; and iPS cells. One of these kinds of undifferentiated cells may be used alone or two or more of these kinds of undifferentiated cells may be used in combination.

Examples of the prokaryotic cells include eubacteria and archaea.

<<<Cell Drying Inhibitor>>>

The cell drying inhibitor has a function of coating the surface of cells to suppress drying of the cells. Examples of the cell drying inhibitor include polyvalent alcohols, gelatinous polysaccharides, and proteins selected from the extracellular matrix.

—Polyvalent Alcohols—

The polyvalent alcohols are not particularly limited so long as the polyvalent alcohols do not damage the cells.

Examples of the polyvalent alcohols include glycerin, diglycerin, diethylene glycol, 1,3-butanediol, 1,2,3-butanetriol, 1,2,4-butanetriol, triethylene glycol, tetraethylene glycol, propylene glycol, and polyethylene glycol. One of these polyvalent alcohols may be used alone or two or more of these polyvalent alcohols may be used in combination. Among these polyvalent alcohols, glycerin is preferable, because toxicity to cells is low and an effect of suppressing drying can be expected with a low amount of addition.

—Gelatinous Polysaccharides—

The gelatinous polysaccharides refer to polysaccharides in a gel state.

The gelatinous polysaccharides are not particularly limited and may be appropriately selected depending on the intended purpose. Examples of the gelatinous polysaccharides include calcium alginate, gellan gum, agarose, guar gum, xanthan gum, carrageenan, pectin, locust bean gum, Tamarind gum, diutan gum, and carboxymethyl cellulose. One of these gelatinous polysaccharides may be used alone or two or more of these gelatinous polysaccharides may be used in combination.

Among these gelatinous polysaccharides, calcium alginate is preferable. Calcium alginate is a salt in which calcium ion is bonded with carboxyl group of alginic acid. Calcium ion is divalent. Hence, calcium ion is bonded (ionically cross-linked) with two carboxyl groups in a manner to bridge the two carboxyl groups, to thicken the viscosity. In this way, calcium alginate can suppress drying of the cell ink. Here, calcium ion is contained in a dispersion medium, and is considered to bond with calcium ion that has become excessive due to drying-induced concentration. Therefore, a function as an osmotic pressure adjustor can also be expected.

—Proteins Selected from Extracellular Matrix—

The proteins selected from the extracellular matrix are not particularly limited and may be appropriately selected depending on the intended purpose. Examples of the proteins selected from the extracellular matrix include collagen, laminin, fibronectin, elastin, and fibrin. One of these proteins may be used alone or two or more of these proteins may be used in combination. Among these proteins, collagen is preferable. There are many kinds of collagens. Collagens are known to thicken depending on the concentration or the temperature. With collagen added in the cell ink, the cell ink can be provided with a trigger for thickening in response to a concentration increase.

<<<Dispersion Medium>>>

As the dispersion medium, a culture medium and a buffer for cell culture are preferable.

A culture medium is a solution that contains components needed for formation and sustainment of a cell tissue, prevents drying, and adjusts the external environment such as the osmotic pressure. Any substance may be appropriately selected and used as the culture medium, so long as the substance is known as a culture medium. When there is no need for immersing the cells in the culture medium liquid all the time, the culture medium may be appropriately removed from the cell suspension.

The buffer is for adjusting pH depending on the cells and the intended purpose. A known buffer may be appropriately selected and used.

<<Step and Unit for Locating Cells>>

The step of locating the cells is a step of discharging a liquid droplet onto a cell adhesive portion to locate the cells over the cell adhesive portion.

In a more specific embodiment, liquid droplets may be discharged onto cell adhesive portions in the pattern to seed the cells onto the cell adhesive portions in the pattern. This makes it possible to form a cell pattern in which the cells adhere to the cell adhesive portions in the pattern.

In the present disclosure, location of a desired number of cells per predetermined position over a substrate may also be referred to as formation of a cell pattern.

In the step of locating the cells, liquid droplets of the cell ink are discharged onto or near the cell adhesive portions in the pattern. As a result, the cells in the liquid droplets that have landed near the cell adhesive portions migrate onto the cell adhesive portions and adhere to the cell adhesive portions.

The conditions such as the positions of cells and the number of cells to be located in the cell pattern can be arbitrarily set by a worker or a user.

For example, by adjusting the timing to discharge liquid droplets depending on the positions of the cell adhesive portions in the pattern, it is possible to adjust the position of the cells that are to adhere to the cell adhesive portions. Here, by adjusting the discharging amount (the number of liquid droplets or the amount of a liquid droplet) of the cell ink and the cell concentration of the cell ink, it is possible to adjust the number of cells that are to adhere to the cell adhesive portions. In this way, by locating the cells over the cell adhesive portions in the pattern, it is possible to form a cell pattern in which a predetermined number of cells are located regularly per predetermined position of the substrate over the substrate.

In a preferred embodiment of the cell tissue producing method of the present disclosure, cell adhesive portions in the pattern are formed, and liquid droplets of a cell ink containing a cell drying inhibitor are discharged onto the cell adhesive portions in the pattern, to form a cell pattern. These steps synergistically produce the effect described below.

Liquid droplets of the cell ink land over a substrate, and the cells are caused to adhere to the cell adhesive portions by flows in the liquid droplets generated upon landing or by migration of the cells. Liquid droplets of the cell ink are much smaller than liquid droplets formed by manual operation. Therefore, the cells adhere to the cell adhesive portions in a very short time. Hence, the cell tissue producing method of the present disclosure can form a cell pattern in a short time. The cell tissue producing method of the present disclosure can provide a cell pattern with a high shape accuracy of the cells being located at a predetermined position. Further, according to the cell tissue producing method of the present disclosure, the probability at which a predetermined number of cells can be located at a predetermined cell adhesive portion or the probability at which the number of cells located is the desired number is high, and the accuracy of locating the desired number of cells is high. Moreover, according to the cell tissue producing method of the present disclosure, the survival rate of the located cells after a predetermined time has passed is also high.

Furthermore, because the cell tissue producing method of the present disclosure can provide a cell pattern with a high shape accuracy, it is possible to form a cell pattern formed of a plurality of cells accurately using a plurality of cells.

<Embodiment of Cell Tissue Producing Method and Apparatus>

A specific embodiment of the cell tissue producing method of the present disclosure and a producing apparatus configured to carry out the producing method will be described below. However, the present disclosure should not be construed as being limited to the embodiment.

The cell tissue producing apparatus includes a stage section, and a liquid droplet discharging head (inkjet head), which is a liquid droplet discharging unit configured to discharge a liquid droplet of the cell suspension.

The stage section is configured to hold a substrate.

The configuration of the liquid droplet discharging head is as described in the above <<Inkjet head for discharging liquid droplets>> section.

FIG. 3A to FIG. 3D illustrate an example of a producing apparatus configured to produce a cell tissue and mounted with the inkjet head for discharging liquid droplets described above.

Figure 3A:
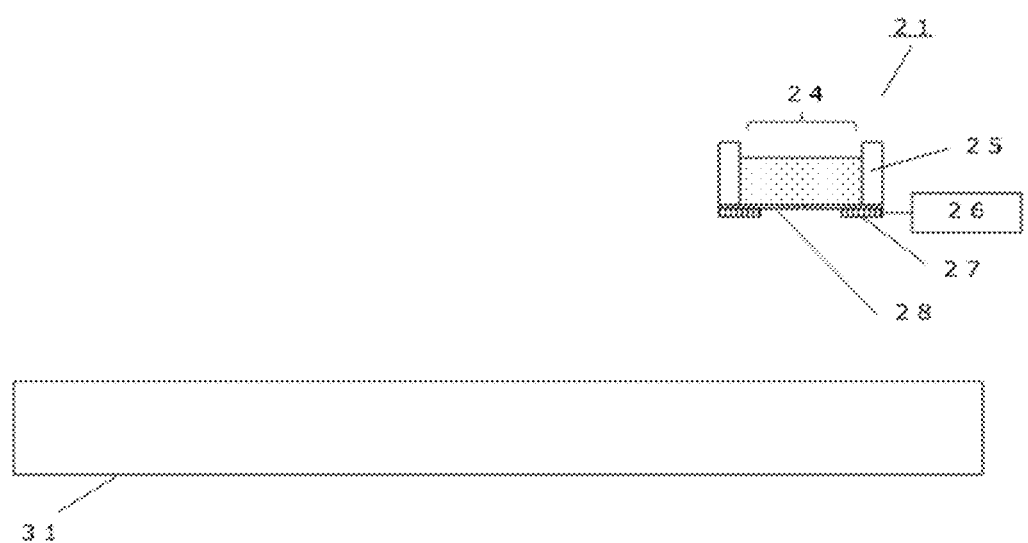
FIG. 3A is a schematic view illustrating an example of a producing apparatus configured to produce a cell tissue.

The cell tissue producing apparatus of FIG. 3A includes a stage section 31 and a liquid droplet discharging head (inkjet head) 21, which is a liquid droplet discharging unit configured to discharge liquid droplets of a cell suspension.

As described above, the liquid droplet discharging head (inkjet head) 21 includes a liquid chamber 25, an exciting unit 27, a driving unit 26, and a membrane 28. The liquid droplet discharging head (inkjet head) 21 is provided with an atmospherically exposed portion 24.

Figure 3B:
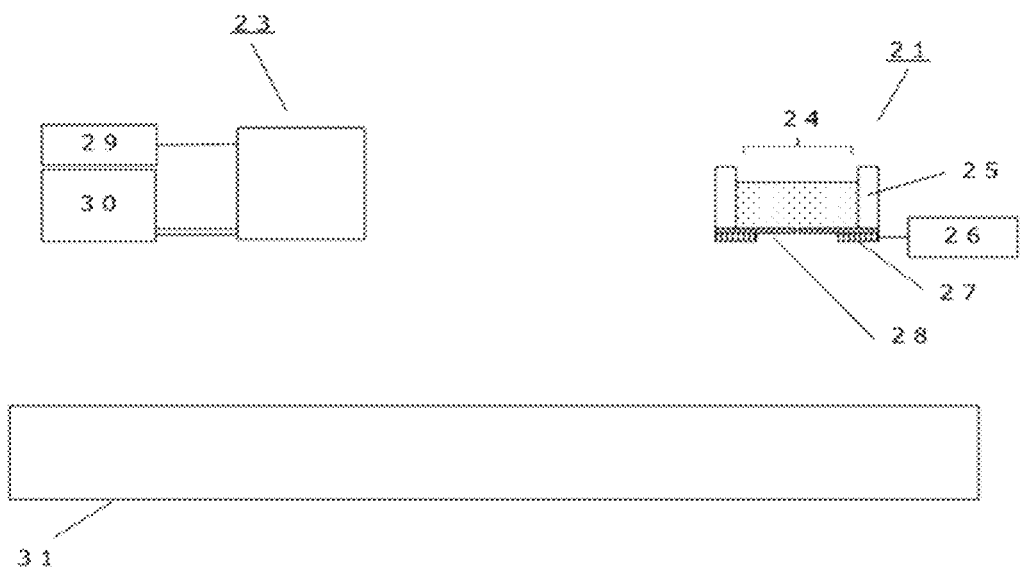
FIG. 3B is a schematic view illustrating another example of a producing apparatus configured to produce a cell tissue.

The cell tissue producing apparatus can also perform formation of cell adhesive portions in the pattern by discharging liquid droplets of a solution containing a cell adhesive material. In this case, the cell tissue producing apparatus includes a liquid droplet discharging head (inkjet head) 23 configured to discharge liquid droplets of the solution containing the cell adhesive material, in addition to the liquid droplet discharging head (inkjet head) 21 configured to discharge liquid droplets of the cell suspension, as illustrated in FIG. 3B. The basic configuration of the liquid droplet discharging head (inkjet head) 23 is the same as the liquid droplet discharging head (inkjet head) 21. In FIG. 3B, the reference sign 29 denotes a driving unit, and the reference sign 30 denotes a liquid chamber configured to retain the solution of the cell adhesive material. The liquid droplet discharging head (inkjet head) 23 includes an exciting unit and a membrane like the liquid droplet discharging head (inkjet head) 21, although not illustrated in the drawing.

Figure 3C:
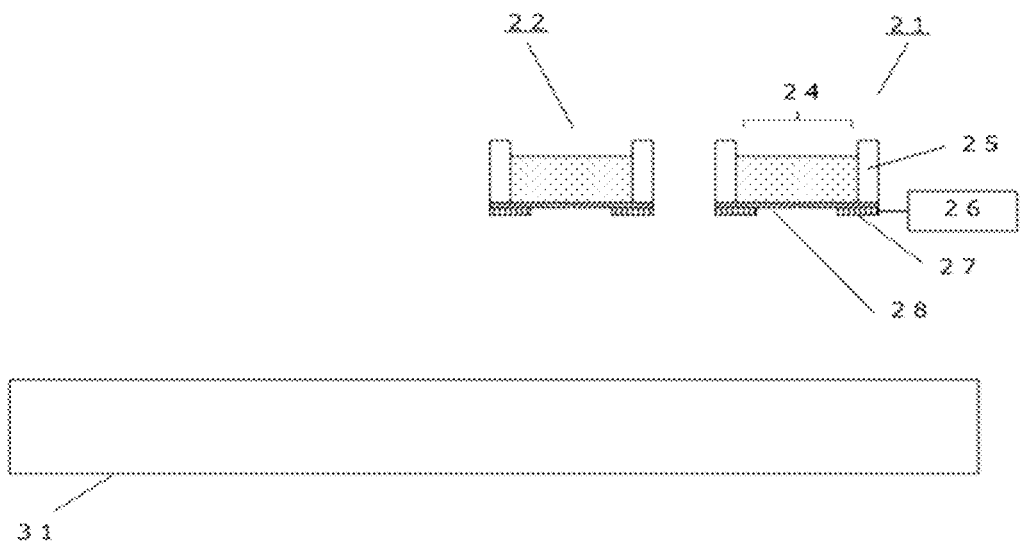
FIG. 3C is a schematic view illustrating another example of a producing apparatus configured to produce a cell tissue.

The cell tissue producing apparatus of the present disclosure can also form a cell pattern formed of two or more kinds of cells. In this case, as illustrated in FIG. 3C, the cell tissue producing apparatus may be provided with a plurality of liquid droplet discharging heads (inkjet heads) 21 configured to discharge liquid droplets of a cell suspension. FIG. 3C illustrates an example in which the cell tissue producing apparatus is provided with two inkjet heads, namely a liquid droplet discharging head (inkjet head) 21 and an inkjet head 22 having the same configuration as the inkjet head 21.

Figure 3D:
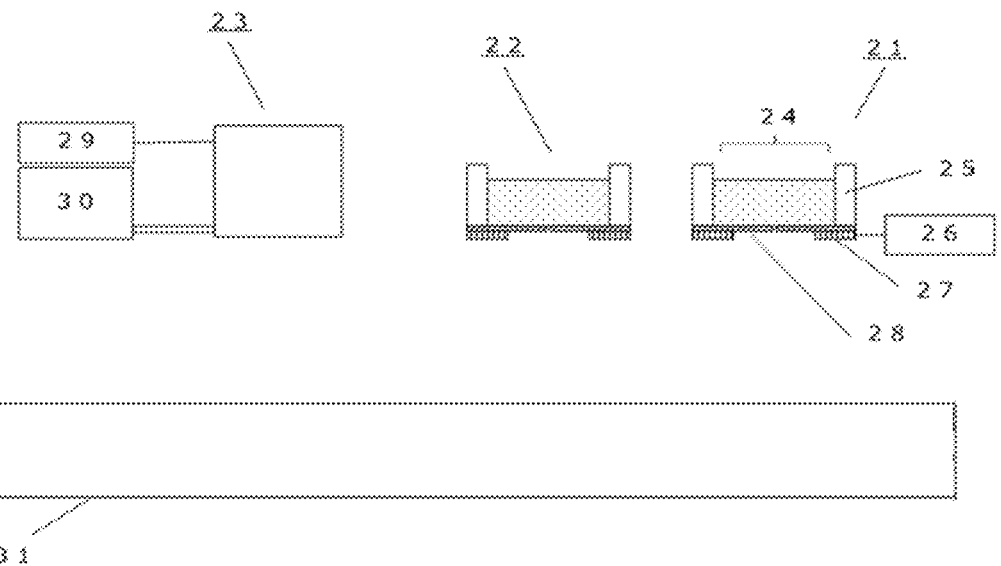
FIG. 3D is a schematic view illustrating another example of a producing apparatus configured to produce a cell tissue.

FIG. 3D illustrates an example of a cell tissue producing apparatus provided with the liquid droplet discharging head (inkjet head) 23, in addition to the two liquid droplet discharging heads (inkjet heads) 21 and 22.

The cell tissue producing apparatus of the present disclosure may include, for example, a holding section configured to hold an inkjet head and a mechanism configured to control a relative position of the stage and the inkjet heads as other units, in addition to the units described above.

Next, a cell tissue producing method using a cell tissue producing apparatus as illustrated in FIG. 3A to FIG. 3D will be specifically described.

The cell tissue producing method will be described with reference to FIG. 4A to FIG. 4F or FIG. 5A to FIG. 5D.

[Step 1 of Forming Cell Adhesive Portions in Pattern (Forming Method by Mask Pattern)]

Figure 4A:
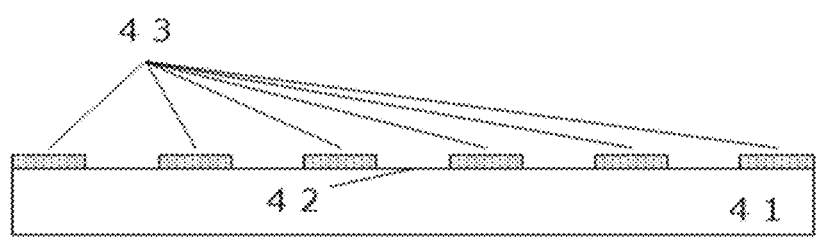
FIG. 4A is a schematic view illustrating an example depicting a cell tissue producing method.

A pattern is drawn on, for example, a film or a weakly adhesive tape with, for example, a laser machine, to form a mask film 43 over a substrate 41 having a cell non-adhesive surface 42. The mask film is pasted over the cell non-adhesive surface (FIG. 4A).

Figure 4B:
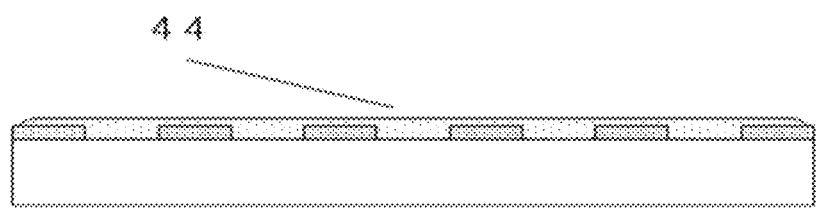
FIG. 4B is a schematic view illustrating an example depicting a cell tissue producing method.
Figure 4C:
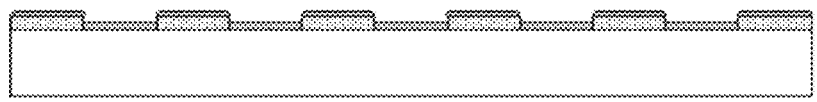
FIG. 4C is a schematic view illustrating an example depicting a cell tissue producing method.

Next, a cell adhesive material 44 is coated (FIG. 4B). As needed, the layer formed of the cell adhesive material may be dried (FIG. 4C).

Figure 4D:
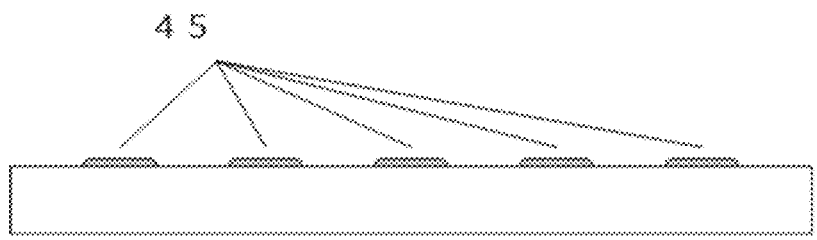
FIG. 4D is a schematic view illustrating an example depicting a cell tissue producing method.

Subsequently, the mask film is peeled. In this way, cell adhesive portions in a pattern 45 formed of the layer of the cell adhesive material can be formed over the substrate having the cell non-adhesive surface (FIG. 4D).

Here, it is preferable to coat the cell adhesive material in a state of being dissolved in, for example, pure water. The content of the cell adhesive material in the cell adhesive material solution is not particularly limited and is preferably from 0.001% by mass through 10% by mass and more preferably form 0.01% by mass through 5% by mass at a mass ratio. In this content range, coating unevenness can be effectively prevented.

It is preferable to form the cell adhesive portions in the pattern by the mask pattern, because the step of forming the cell adhesive portions is simple and the cell adhesive portions to be formed become solid flat films, which have an excellent adhesiveness with the cells.

[Step 2 of Forming Cell Adhesive Portions in Pattern (Forming Method by Inkjet)]

—Preparation of Cell Adhesive Material Ink—

The cell adhesive material is dissolved in, for example, pure water, to prepare a cell adhesive material ink. Here, the content of the cell adhesive material in the cell adhesive material solution is not particularly limited and is preferably from 0.001% by mass through 5% by mass and more preferably from 0.005% by mass through 1% by mass at a mass ratio. In this content range, the cell adhesive function can be sufficiently expressed, and liquid droplets can be favorably discharged by the inkjet method.

As needed, the cell adhesive material ink may contain other additive materials such as a humectant, a dispersant, and a pH adjustor.

—Step of Forming Pattern of Cell Adhesive Portions by Inkjet—

As a producing apparatus, an apparatus including the cell adhesive material discharging head 23 illustrated in FIG. 3B can be used.

Figure 5A:
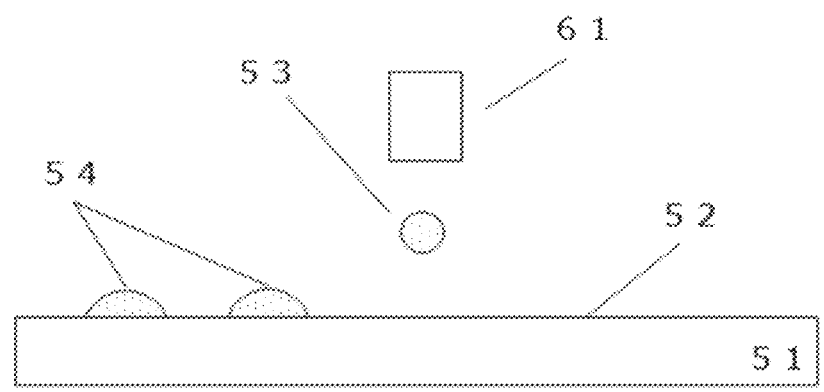
FIG. 5A is a schematic view illustrating another example depicting a cell tissue producing method.
Figure 5B:
FIG. 5B is a schematic view illustrating another example depicting a cell tissue producing method.

As illustrated in FIG. 5A and FIG. 5B, a pattern 55 of cell adhesive portions formed of the cell adhesive material is formed over a substrate 51 having a cell non-adhesive surface 52. The cell adhesive material ink is filled in the liquid chamber of a cell adhesive material discharging head 61 and liquid droplets 53 of the cell adhesive material ink are discharged onto the substrate 51 having the cell non-adhesive surface 52 (FIG. 5A). In discharging the liquid droplets 53, for example, the discharging timing and the discharging amount of a liquid droplet are adjusted, to form cell adhesive portions having a desired pattern shape. In this way, cell adhesive portions 55 in the pattern can be formed over the substrate having the cell non-adhesive surface (FIG. 5B).

As illustrated in FIG. 6A to FIG. 6F, cell adhesive portions in a pattern may be formed by transfer from a printing plate (contact printing method).

Figure 6A:
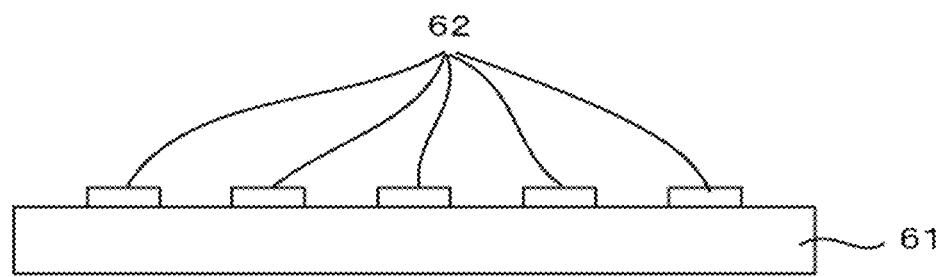
FIG. 6A is a schematic view illustrating another example depicting a cell tissue producing method (contact printing method)
Figure 6B:
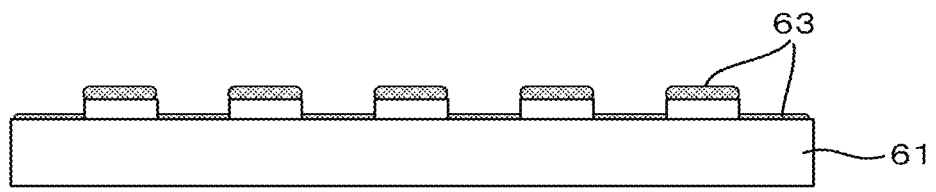
FIG. 6B is a schematic view illustrating another example depicting a cell tissue producing method (contact printing method)
Figure 6C:
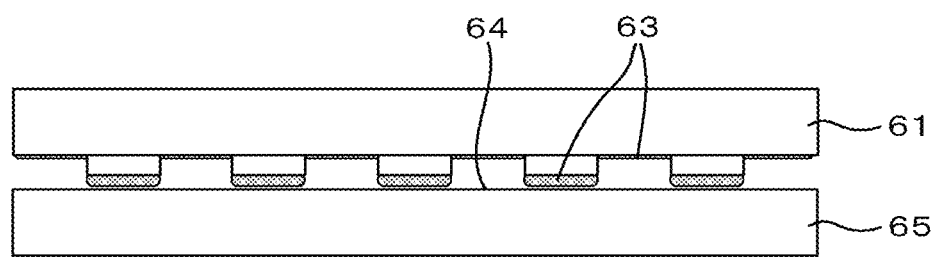
FIG. 6C is a schematic view illustrating another example depicting a cell tissue producing method (contact printing method)
Figure 6D:
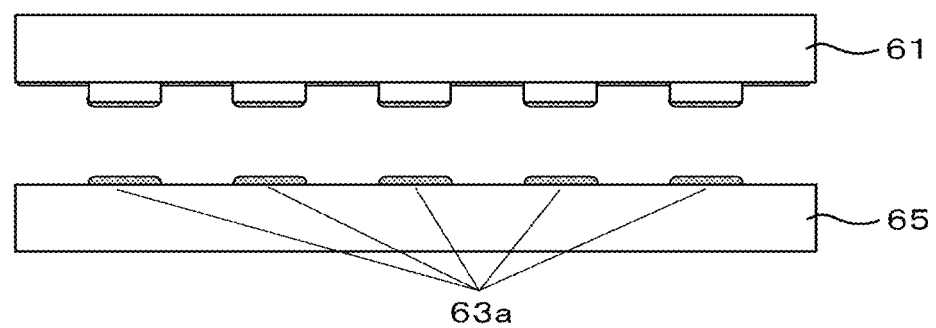
FIG. 6D is a schematic view illustrating another example depicting a cell tissue producing method (contact printing method)
Figure 6E:
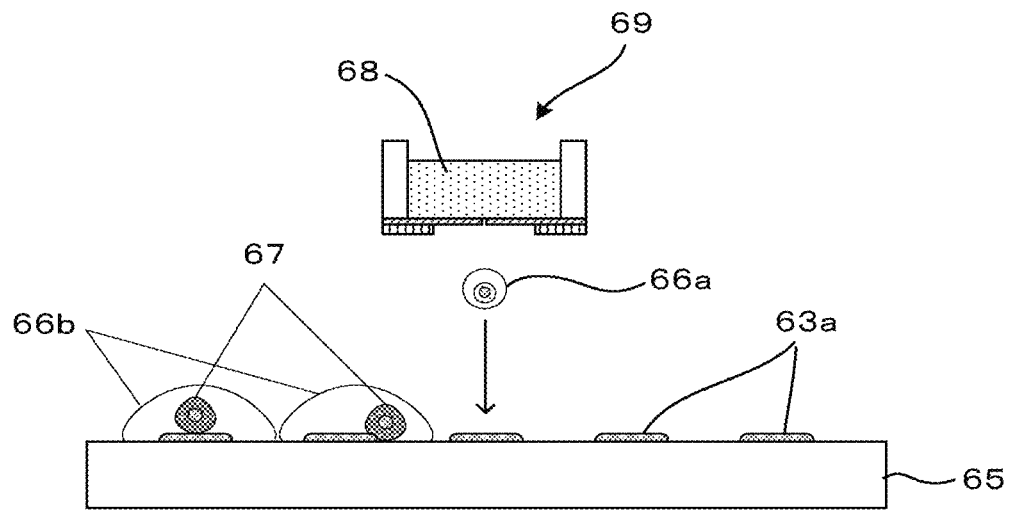
FIG. 6E is a schematic view illustrating another example depicting a cell tissue producing method (contact printing method)
Figure 6F:
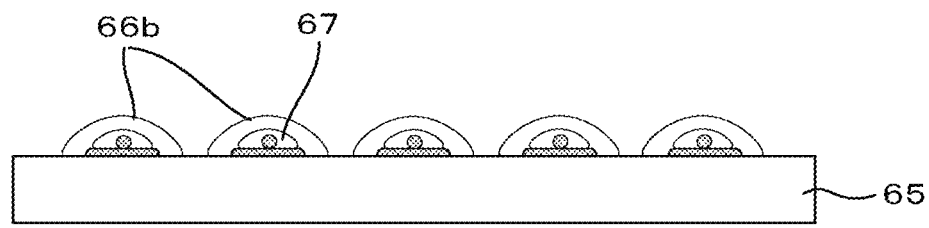
FIG. 6F is a schematic view illustrating another example depicting a cell tissue producing method (contact printing method)
Figure 7A:
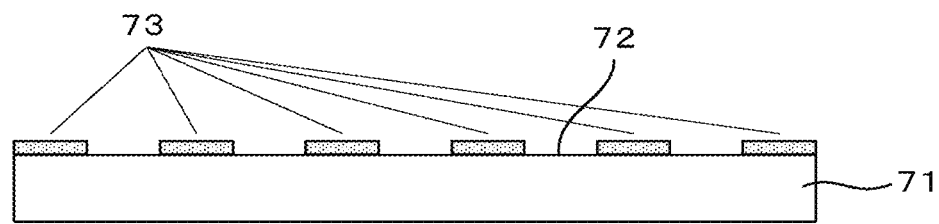
FIG. 7A is a schematic view illustrating another example depicting a cell tissue producing method (negative printing method (mask))
Figure 7B:
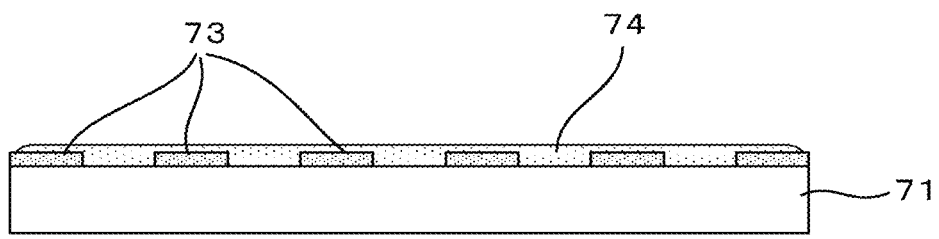
FIG. 7B is a schematic view illustrating another example depicting a cell tissue producing method (negative printing method (mask))
Figure 7C:
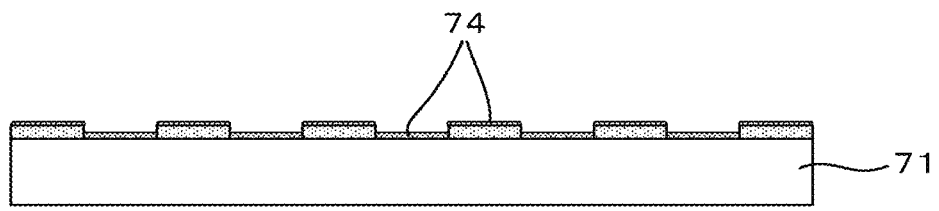
FIG. 7C is a schematic view illustrating another example depicting a cell tissue producing method (negative printing method (mask))
Figure 7D:
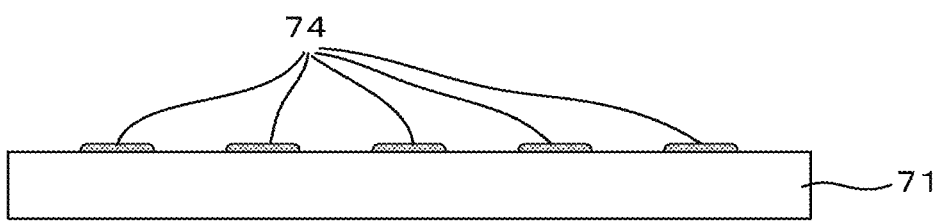
FIG. 7D is a schematic view illustrating another example depicting a cell tissue producing method (negative printing method (mask))
Figure 7E:
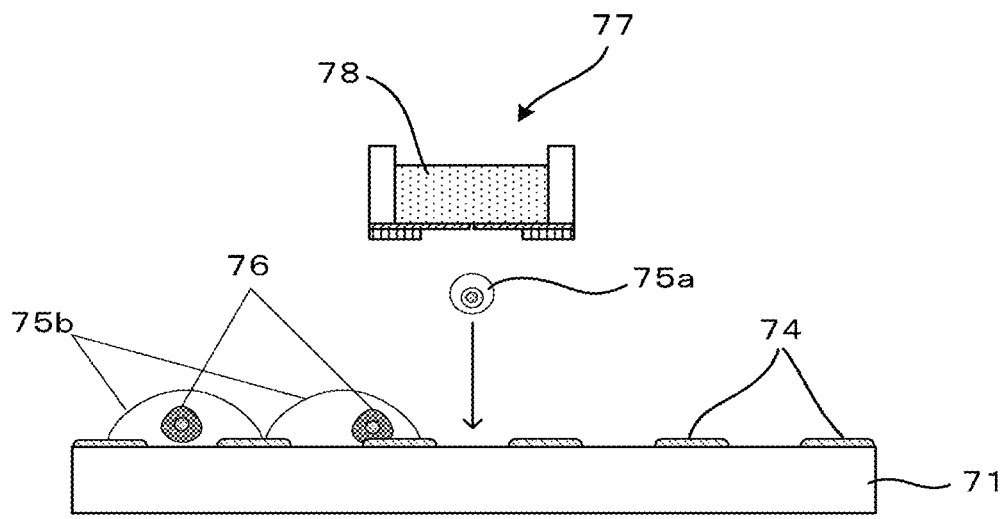
FIG. 7E is a schematic view illustrating another example depicting a cell tissue producing method (negative printing method (mask))
Figure 7F:
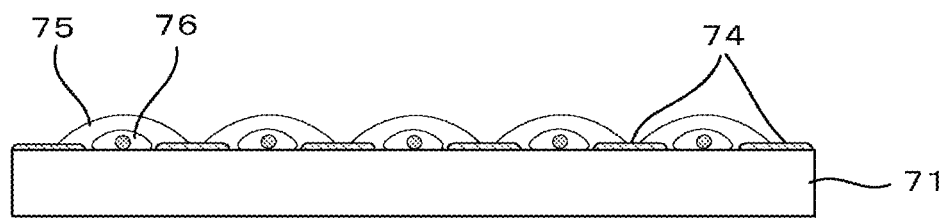
FIG. 7F is a schematic view illustrating another example depicting a cell tissue producing method (negative printing method (mask))
Figure 8A:
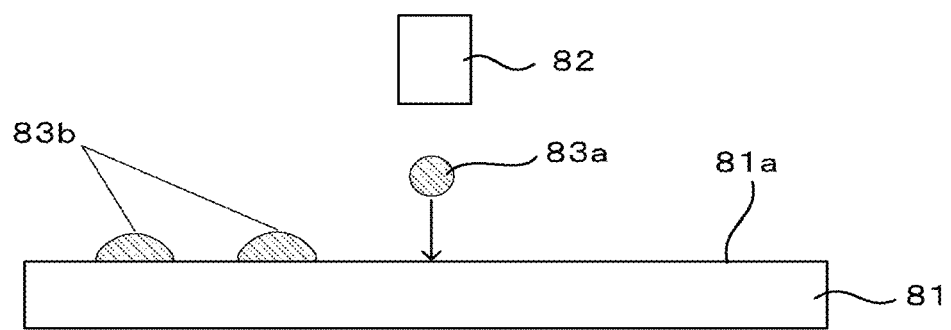
FIG. 8A is a schematic view illustrating another example depicting a cell tissue producing method (negative printing method (IJ))
Figure 8B:
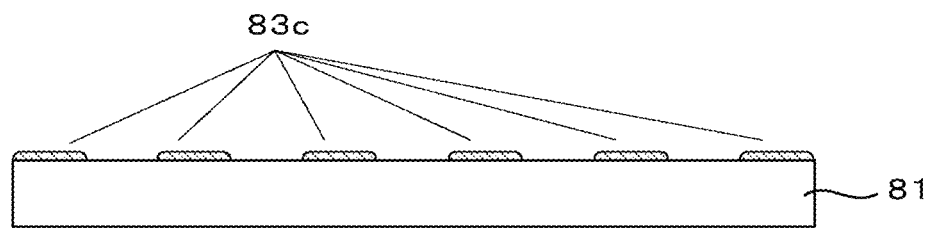
FIG. 8B is a schematic view illustrating another example depicting a cell tissue producing method (negative printing method (IJ))
Figure 8C:
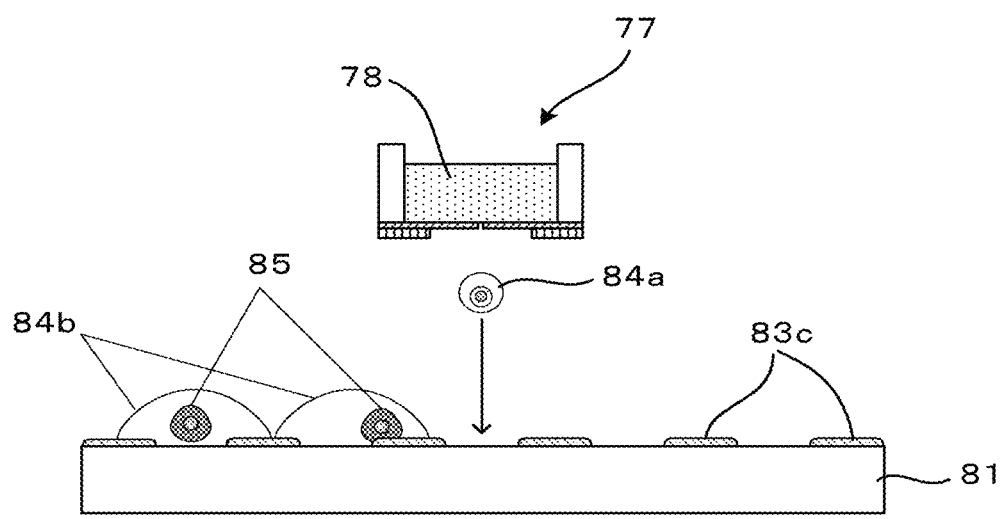
FIG. 8C is a schematic view illustrating another example depicting a cell tissue producing method (negative printing method (IJ))
Figure 8D:
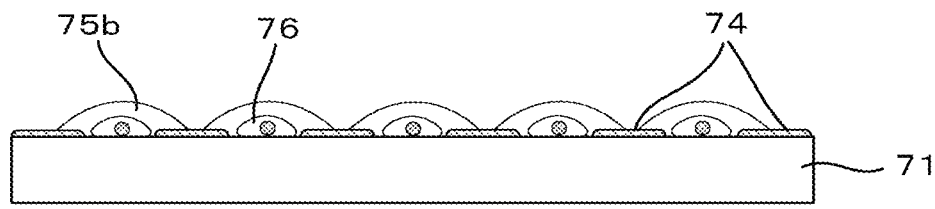
FIG. 8D is a schematic view illustrating another example depicting a cell tissue producing method (negative printing method (IJ))
Figure 9A:
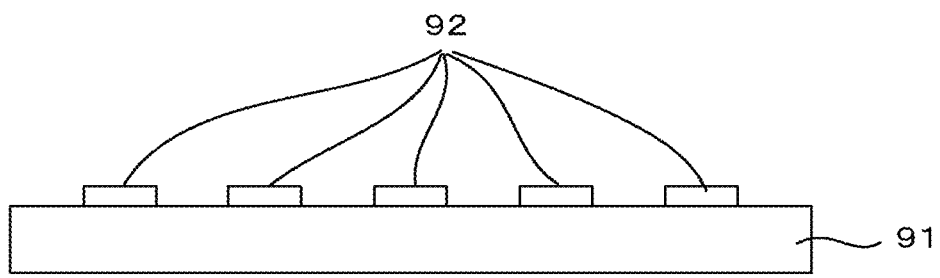
FIG. 9A is a schematic view illustrating another example depicting a cell tissue producing method (negative printing method (contact))
Figure 9B:
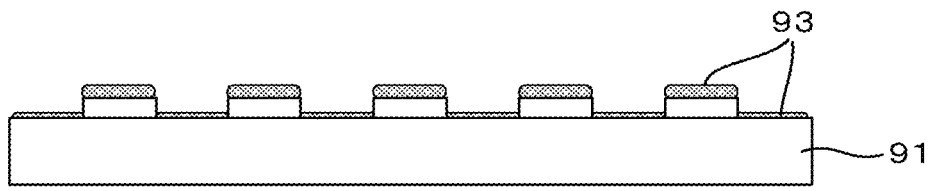
FIG. 9B is a schematic view illustrating another example depicting a cell tissue producing method (negative printing method (contact))
Figure 9C:
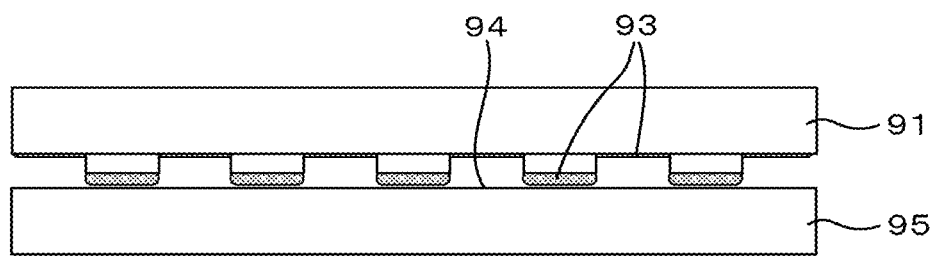
FIG. 9C is a schematic view illustrating another example depicting a cell tissue producing method (negative printing method (contact))
Figure 9D:
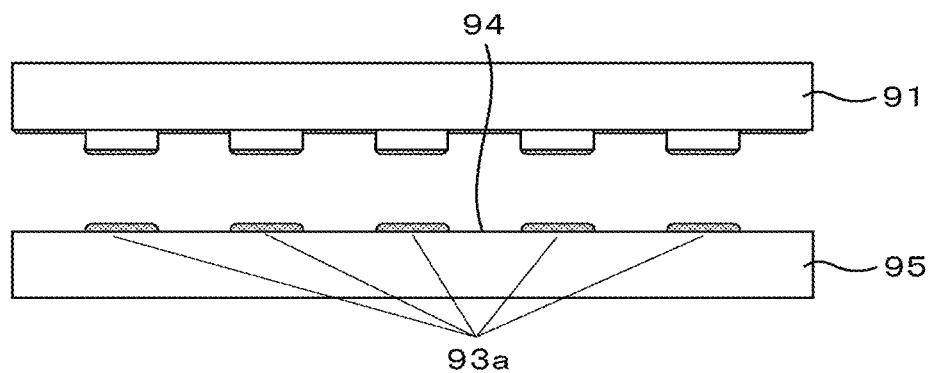
FIG. 9D is a schematic view illustrating another example depicting a cell tissue producing method (negative printing method (contact))
Figure 9E:
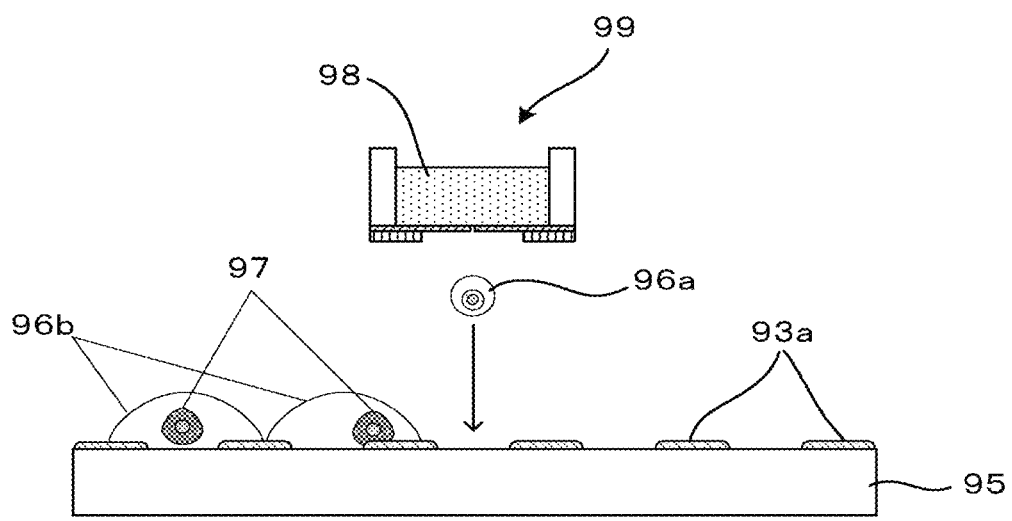
FIG. 9E is a schematic view illustrating another example depicting a cell tissue producing method (negative printing method (contact))
Figure 9F:
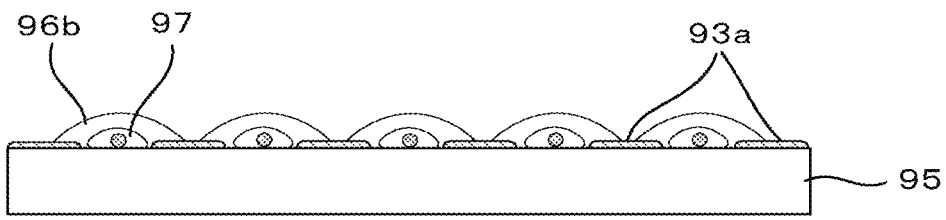
FIG. 9F is a schematic view illustrating another example depicting a cell tissue producing method (negative printing method (contact))
Figure 10A:
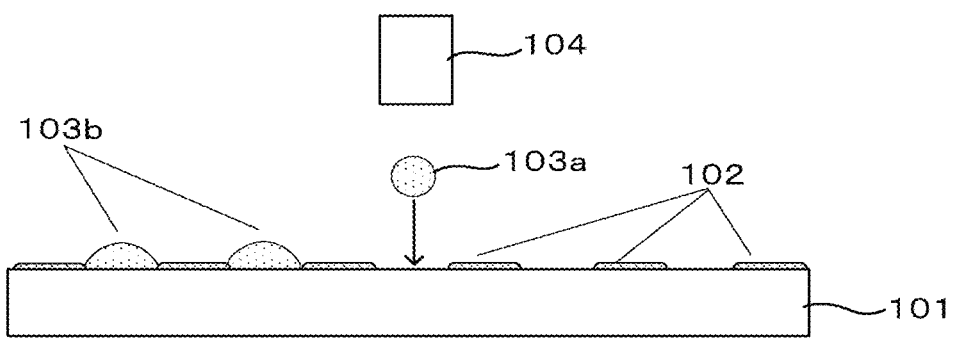
FIG. 10A is a schematic view illustrating another example depicting a cell tissue producing method (latent image+ negative printing method (IJ+IJ))
Figure 10B:
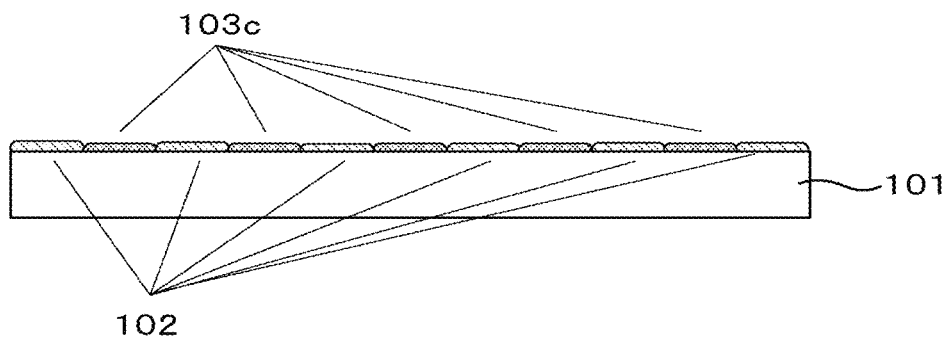
FIG. 10B is a schematic view illustrating another example depicting a cell tissue producing method (latent image+ negative printing method (IJ+IJ))
Figure 10C:
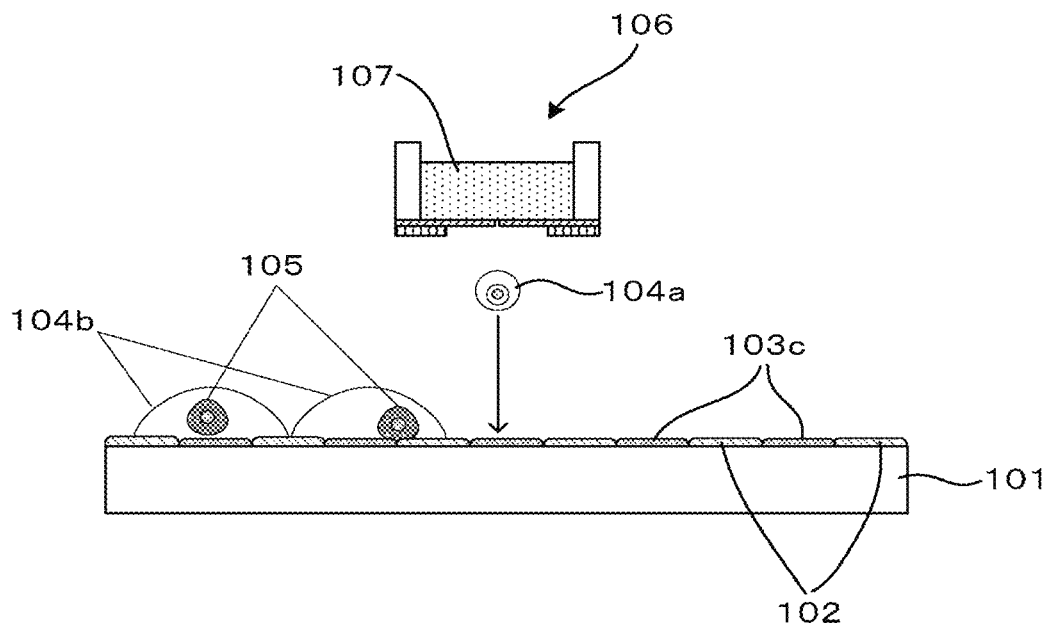
FIG. 10C is a schematic view illustrating another example depicting a cell tissue producing method (latent image+ negative printing method (IJ+IJ))
Figure 10D:
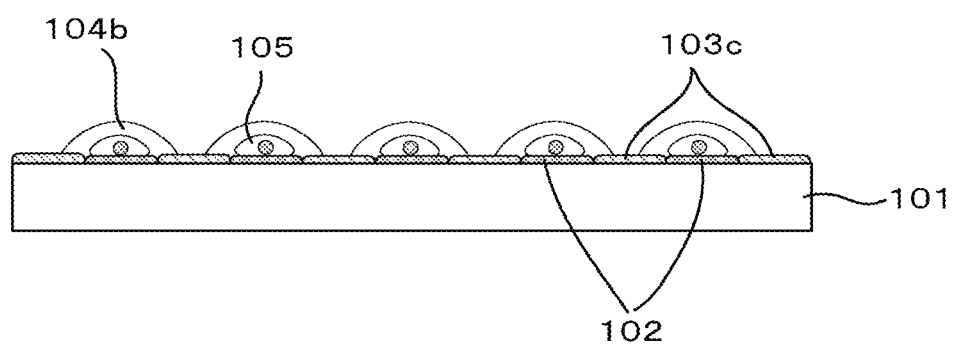
FIG. 10D is a schematic view illustrating another example depicting a cell tissue producing method (latent image+ negative printing method (IJ+IJ))

The process is the same as in the above-described step of forming a pattern of cell adhesive portions by inkjet, except that a cell adhesive material 63 is coated over a printing plate 61, to transfer the cell adhesive material 63 onto a substrate 65 having a cell non-adhesive surface 64 and form a cell adhesive material pattern 63a as illustrated in FIG. 6B.

In FIG. 6A to FIG. 6F, the reference sign 66a denotes a flying liquid droplet, the reference sign 66b denotes a landed liquid droplet, the reference sign 67 denotes a cell, the reference sign 68 denotes a cell suspension, and the reference sign 69 denotes a cell discharging head.

The material used as the printing plate is not particularly limited so long as the printing plate can keep the cell adhesive material. However, typically, a softer material than a base material is preferred because such a material has a better followability during transfer. The pressure during transfer is also not particularly limited so long as a pattern over the printing plate is not crushed.

[Cell Pattern Forming Step]

—Preparation of Cell Suspension (Cell Ink)—

A cell drying inhibitor is dissolved in a dispersion medium, to prepare a cell ink dispersion medium. Here, the content of the cell drying inhibitor is not particularly limited and is preferably from 0.001% by mass through 20% by mass and more preferably from 0.01% by mass through 10% by mass as the mass ratio of the cell drying inhibitor in the cell suspension. In this content range, the drying inhibiting effect can be exhibited and is lowly damaging to the cells, although depending on the kind of the cells. Next, cells are dispersed in the cell ink dispersion medium and gently stirred by pipetting, to obtain a cell ink. Here, the content of cells in the cell suspension is preferably from $5\times10^5$ cells/mL through $1\times10^8$ cells/mL and more preferably from $1\times10^6$ cells/mL through $5\times10^7$ cells/mL. In this content range, the cell density does not happen to be low and there is no difficulty with performing discharging by the inkjet method.

The environment temperature in the cell ink preparing step is preferably from 4 degrees C. through 40 degrees C. and more preferably from 15 degrees C. through 37 degrees C. Cells will not die immediately when the temperature exceeds 37 degrees C. However, when the temperature greatly exceeds 37 degrees C. or the cells are exposed to such a temperature for a long time, damage on the cells is feared. Further, an environment temperature below 4 degrees C. is not lethally influential to the cells, but reduces the activity of the cells and tends to increase the time needed for the cells to adhere according to this process.

—Formation of Cell Pattern—

Figure 4E:
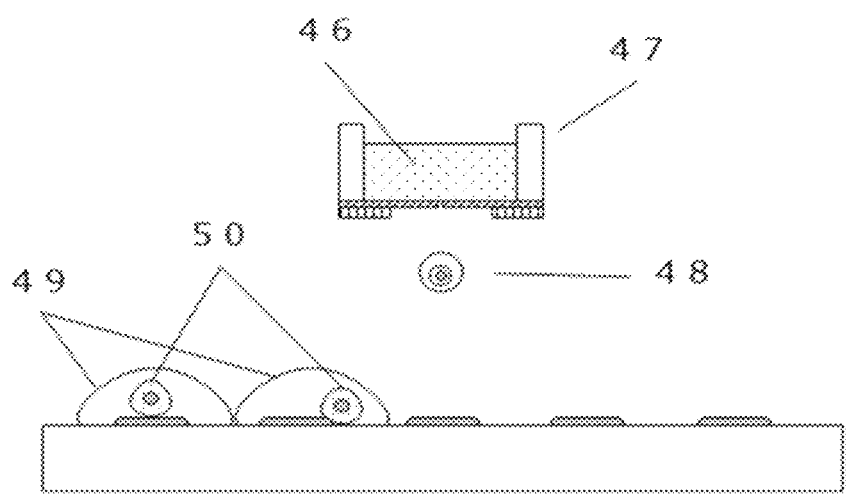
FIG. 4E is a schematic view illustrating an example depicting a cell tissue producing method.
Figure 4F:
FIG. 4F is a schematic view illustrating an example depicting a cell tissue producing method.

As illustrated in FIG. 4E, the cell ink 46 is discharged onto the substrate over which the cell adhesive portions in the pattern 45 are formed, to locate the cell ink 46. The cell ink 46 is filled in the liquid chamber of a cell discharging head 47 and discharged along the cell adhesive portions in the pattern 45 formed over the substrate. Here, the driving signal is not particularly limited so long as the cell ink can be discharged through the nozzle. Because the cells are dispersed in an ink liquid droplet, it is difficult to control the positions of the cells after landing. However, because the cell adhesive portions have the pattern, cells that have landed near the cell adhesive portions can migrate to the cell adhesive portions and adhere to the cell adhesive portions. In FIG. 4E, the reference sign 48 denotes a flying liquid droplet, the reference sign 49 denotes a liquid droplet that has landed, and the reference sign 50 denotes a cell. Hence, a cell pattern in which the cells are regularly located at predetermined positions over the substrate can be formed (FIG. 4F).

Figure 5C:
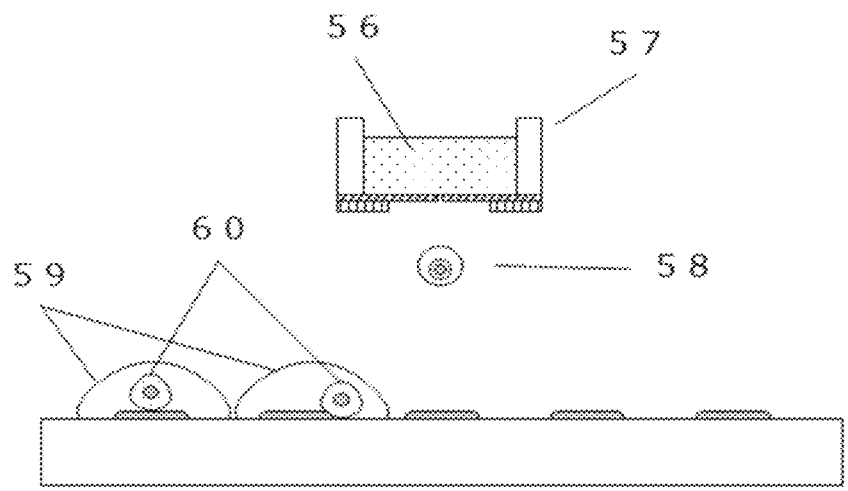
FIG. 5C is a schematic view illustrating another example depicting a cell tissue producing method.

In FIG. 5C, a cell pattern can be formed likewise.

Figure 5D:
FIG. 5D is a schematic view illustrating another example depicting a cell tissue producing method.

As illustrated in FIG. 5C, the cell ink 56 is discharged onto a substrate over which cell adhesive portions in the pattern 55 are formed, to locate the cell ink 56. The cell ink 56 is filled in the liquid chamber of a cell discharging head 57 and discharged along the cell adhesive portions in the pattern 55 formed over the substrate. Cells that have landed near the cell adhesive portions migrate to the cell adhesive portions and adhere to the cell adhesive portions. In FIG. 5C, the reference sign 58 denotes a flying liquid droplet, the reference sign 59 denotes a liquid droplet that has landed, and the reference sign 60 denotes a cell. Hence, a cell pattern in which the cells are regularly located at predetermined positions over the substrate can be formed (FIG. 5D).

In FIG. 4E and FIG. 5C, by changing the number of liquid droplets to be discharged or by changing the cell dispersion concentration in the cell ink, it is possible to control the number of cells to be located per unit area of the cell pattern. By controlling the number of cells per unit area, it is possible to arbitrarily design interactions such as adhesion between cells and exchange of proteins. Hence, it is possible to provide a potential not only for evaluation of cells merely, but also for evaluation of the function as a cell tissue. Further, because minute liquid droplets are caused to land by inkjet, the time that is to be taken, after the liquid droplets have landed, for the cells to land over the substrate, migrate to the cell adhesive portions, and adhere to the cell adhesive portions can be made very short. Furthermore, according to the present disclosure, it is possible to discharge liquid droplets of the cell ink stably. However, even if discharging becomes unstable, it is possible to perform discharging stably again, by performing stirring in the liquid chamber, including the portion near the nozzle of the inkjet head.

Specific Example of Cell Tissue Over which Cell Pattern is Formed

A specific example of a cell tissue formed according to the cell tissue producing method of the present disclosure will be described below.

Cell adhesive portion dots with a diameter (ϕ) of 150 micrometers were formed over a substrate. Liquid droplets of a cell ink were discharged toward each dot such that one cell would be located per dot.

Figure 11A:
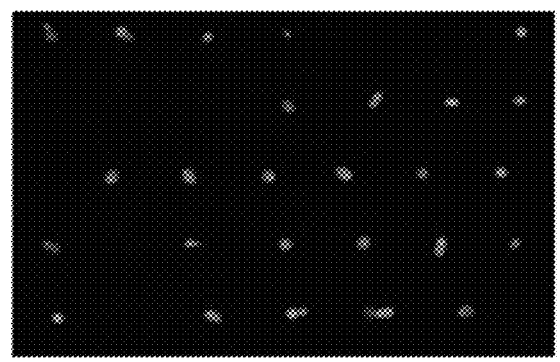
FIG. 11A is an image illustrating a formed example of a cell pattern in which one or two cells are located per predetermined position over a substrate.

As the cells, NIH/3T3 was used. FIG. 11A illustrates an image of the result of locating cells, trying to locate one cell per dot.

Figure 11B:
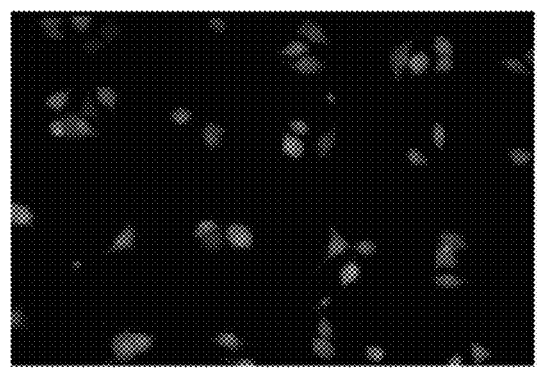
FIG. 11B is an image illustrating a formed example of a cell pattern in which three or four cells are located per predetermined position over a substrate.

FIG. 11B illustrates an image of the result of locating cells, trying to locate three cells per dot in the same manner.

Figure 11C:
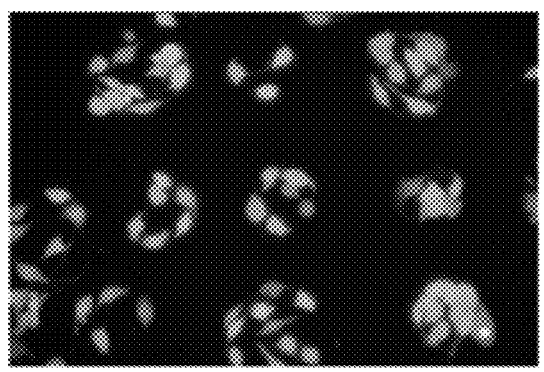
FIG. 11C is an image illustrating a formed example of a cell pattern in which about ten cells are located per predetermined position over a substrate.

FIG. 11C illustrates an image of the result of locating cells, trying to locate ten cells per dot in the same manner.

Figure 12A:
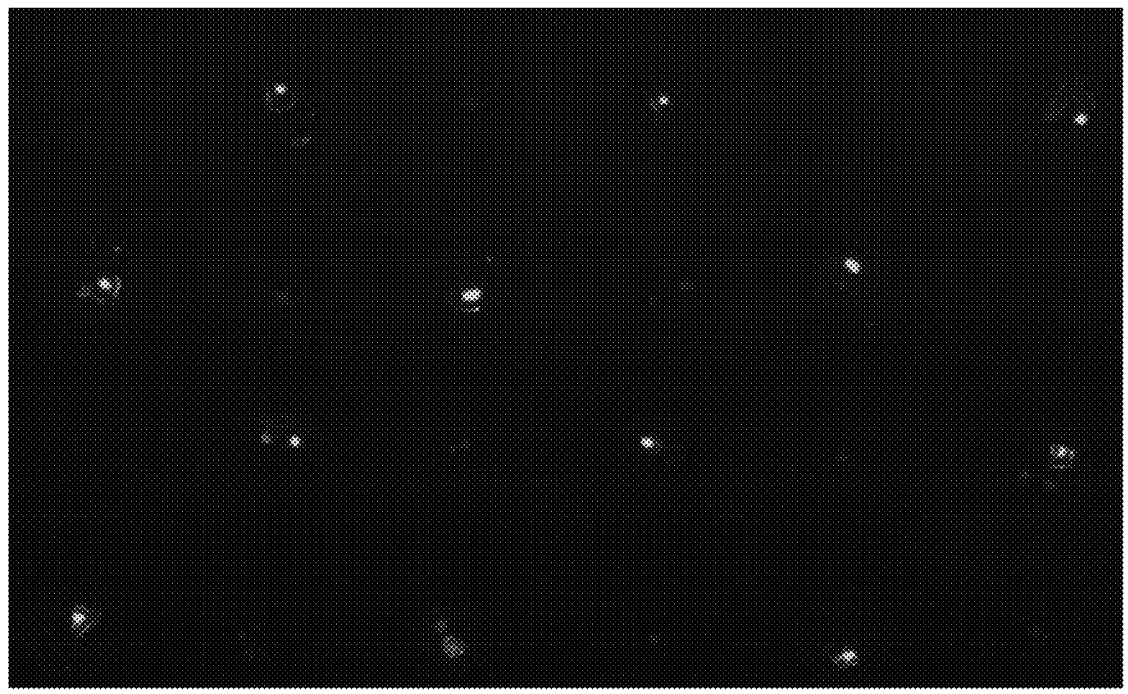
FIG. 12A is an image illustrating a formed example of a cell pattern in which two kinds of cells are located per predetermined position over a substrate.

FIG. 12A illustrates an image of the result of locating two kinds of cells, each kind of cells regularly (a cell pattern formed of two kinds of cells).

As the cells, NIH/3T3 and NHDF were used.

Figure 12B:
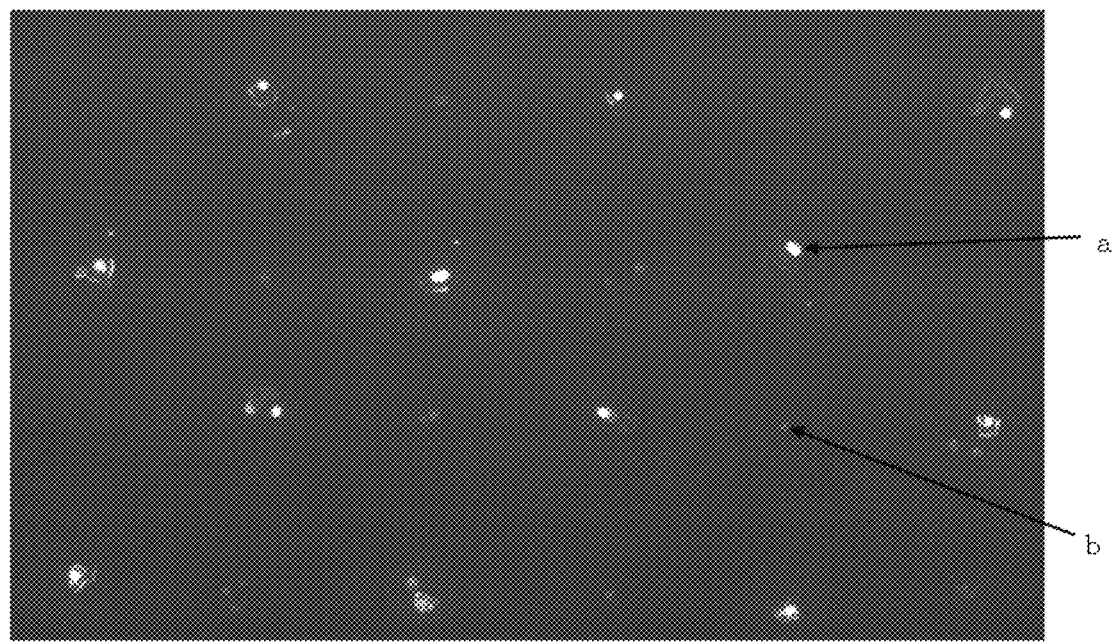
FIG. 12B is an image illustrating the cell pattern formed of two kinds of cells of FIG. 12A.

The image of FIG. 12A was originally a colored image with color separation by green and blue on a black background. Hence, the state of how cells of each kind were located was easily recognized visually. However, FIG. 12A attached is displayed in black and white. Hence, FIG. 12B is attached as a supplementary illustration. In FIG. 12B, the reference signs a and b denote the different two kinds of cells respectively.

<Non-Transitory Recording Medium Storing Cell Tissue Producing Program>

The non-transitory recording medium storing a cell tissue producing program stores a cell tissue producing program that causes the cell tissue producing apparatus of the present disclosure to execute the cell tissue producing method, using, for example, computers as hardware resources.

The process according to the cell tissue producing program stored in the non-transitory recording medium can be executed, using a computer including a control unit constituting the cell tissue producing apparatus described above (the producing apparatus of, for example, FIG. 3A to FIG. 3D).

Figure 13:
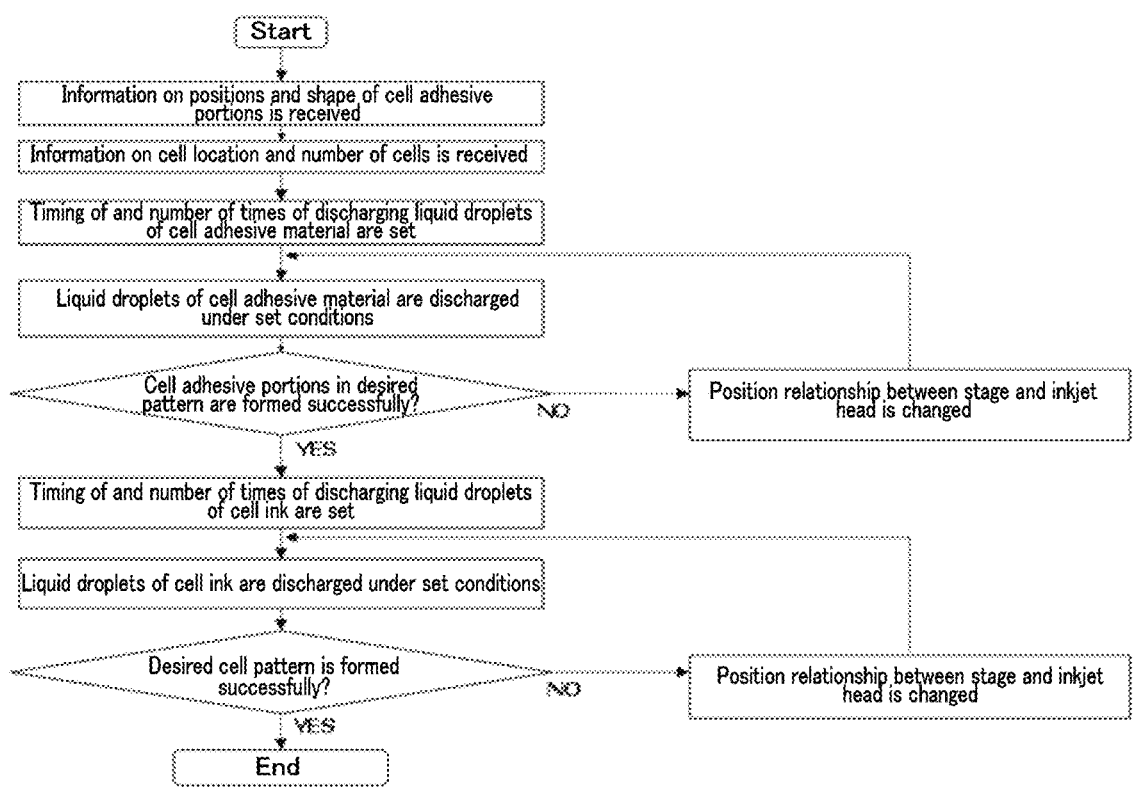
FIG. 13 is a flowchart illustrating an example of a process executed by a cell tissue producing apparatus according to a cell tissue producing program stored in a non-transitory recording medium.

An example of the process according to the cell tissue producing program stored in the non-transitory recording medium of the present disclosure will be presented. FIG. 13 is a flowchart illustrating an example of a process executed by the cell tissue producing apparatus according to the cell tissue producing program stored in the non-transitory recording medium.

It is also possible to locate cells in an optional manner, by patterning the cell non-adhesive material in the same manner as patterning the cell adhesive material as described above.

For example, as illustrated in FIG. 7A to FIG. 7F (negative printing method (mask)), FIG. 8A to FIG. 8D (negative printing method (IJ)), and FIG. 9A to FIG. 9F (negative printing method (contact)), by forming a pattern of the cell adhesive material over a base material (71, 81, 95) having a cell adhesive surface (72, 81a, 94), it is possible to locate cells at positions other than cell non-adhesive material patterned portions (74, 83c, 93a).

As illustrated in FIG. 10A to FIG. 10D, it is possible to locate cells regardless of the property of a surface of a base material 101, by locating a cell non-adhesive material pattern 102 (latent image) and a cell adhesive material pattern 103c (negative printing) over the base substrate 101, using, for example, an inkjet (IJ) device.

EXAMPLES

The present disclosure will be described below more specifically by way of Examples. However, the present disclosure should not construed as being limited to these Examples.

Example 1

<Formation of Cell Adhesive Portions in Pattern>
The followings were prepared in order to form a cell non-adhesive surface over a glass slide. A sodium alginate solution was prepared by dissolving sodium alginate (SKAT ONE, available from Kimica Corporation) in distilled water at a mass ratio of 2% by mass. Further, a calcium chloride solution was prepared by dissolving calcium chloride dehydrate (available from Wako Pure Chemical Industries Ltd.) in distilled water at 100 mmol/L. The sodium alginate solution and the calcium chloride solution were mixed at a mass ratio of 1:1 and coated over the glass slide, to form a calcium alginate gel layer as a cell non-adhesive surface layer.

Then, using a laser machine (H10-106QW J80-8SS42 HIPPO, available from Spectra-Physics, Inc.), holes having a diameter ($\phi$) of 100 micrometers were opened in a polyimide film having a thickness of 50 micrometers (3-1966-03, available from As One Corporation) at a pitch of 300 micrometers, to form a mask film. The substrate having the cell non-adhesive surface was covered with the mask film formed. As a cell adhesive material, fibronectin (F-2006, fibronectin from human plasma, available from SIGMA-ALDRICH Co., LLC.) was dissolved in distilled water at a mass ratio of 0.10% by mass, to prepare a cell adhesive material solution. The cell adhesive material solution was coated and dried over the substrate that had the cell non-adhesive surface and over which the mask film was pasted. Subsequently, the mask film was peeled, to form a pattern layer of the cell adhesive material (cell adhesive portions in the pattern) over the substrate having the cell non-adhesive surface.

<Preparation of Cell Ink>
Cells were stained in order to evaluate the cell pattern formed. A green fluorescent dye (product name: CELL TRACKER GREEN, available from Life Technologies Corporation) was dissolved in dimethyl sulfoxide (hereinafter, referred to as "DMSO") at a concentration of 10 mmol/L (mM), and mixed with a serum-free Dulbecco's modified Eagle's medium (available from Life Technologies Corporation), to prepare a green fluorescent dye-containing serum-free medium having a concentration of 10 micromoles/L (micromol). Next, the green fluorescent dye-containing serum-free medium (5 mL) was added in a dish of cultured NIH/3T3 cells (CLONE 5611, JCRB Cell Bank) and the resultant was cultured in an incubator (KM-CC17RU2, available from Panasonic Corporation, in a 5% by volume $CO_2$ environment at 37 degrees C.) for 30 minutes. Subsequently, the supernatant was removed using an aspirator. A phosphate buffered saline (available from Life Technologies Corporation, hereinafter may also be referred to as PBS (−)) (5 mL) was added in the dish and then aspirated with an aspirator, to wash the surface. The washing operation with PBS (−) was repeated twice, and then a 0.05% by mass trypsin-0.05% by mass EDTA solution (available from Life Technologies Corporation) was added in an amount of 2 mL per dish. Next, the resultant was heated in an incubator for 5 minutes, and after the cells were stripped from the dish, D-MEM (4 mL) containing a 10% by mass fetal bovine serum (hereinafter, may also be referred to as "FBS") and a 1% by mass antibiotic (ANTIBIOTIC-ANTIMYCOTIC MIXED STOCK SOLUTION (100×), available from Nacalai Tesque Inc.) was added in the dish. Next, the cell suspension in which trypsin was deactivated was removed into a 50 mL centrifuge tube for centrifugation (product name: H-19FM, available from KOKUSAN Co., Ltd., at 1,200 rpm, for 5 minutes, at 5 degrees C.), and then the supernatant was removed with an aspirator. After the removal, the D-MEM (2 mL) containing the 10% by mass FBS and the 1% by mass antibiotic was added in the centrifuge tube, followed by gentle pipetting, to obtain a cell suspension in which the cells were dispersed. The cell suspension (10 microliters) was taken out into an Eppendorf tube, into which a culture medium (70 microliters) was added. Subsequently, the resultant (10 microliters) was taken out into another Eppendorf tube, into which a 0.4% by mass Trypan blue stain (10 microliters) was added, followed by pipetting. The stained cell suspension (10 microliters) was taken out and poured onto a plastic slide formed of PMMA. Using a product named: COUNTESS AUTOMATED CELL COUNTER (available from Invitrogen), the number of cells was counted to obtain the number of cells, to obtain a cell suspension for which the number of cells was counted. PBS (−) was used as a dispersion medium. Glycerin (molecular biology grade, available from Wako Pure Chemical Industries Ltd.) serving as a cell drying inhibitor was dissolved in the PBS (−) at a mass ratio of 0.5% by mass, and the NIH/3T3 cell suspension was dispersed in the dispersion medium at $6\times10^6$ cells/mL, to obtain a cell ink.

<Formation of Cell Pattern>
The cell ink was filled in the liquid chamber of the cell discharging head of the cell tissue producing apparatus of FIG. 3A. Next, the cell ink was dropped onto twenty dots of the cell adhesive portion dots in the pattern produced above, by three liquid droplets per dot (having a diameter ($\phi$) of 100 micrometers) (intending to locate six cells per dot). Further, the cell ink was dropped onto twenty dots, by five liquid droplets per dot (intending to locate ten cells per dot).

The cell adhesive portions were left to stand still for 10 minutes from when the final liquid droplet of the cell ink had landed, and subsequently the D-MEM containing the 10% by mass FBS and the 1% by mass antibiotic was calmly added.

In this way, a cell tissue over which a cell pattern was formed was produced.

<Evaluation of Cell Pattern>

The cell pattern over the obtained cell tissue was evaluated in the manners described below. The evaluation results are presented in Table 1 below.

[Initial Cell Adhesion Time]

Whether the cells had adhered to the cell adhesive portions in the pattern through being left to stand still for 10 minutes was evaluated according to the criteria described below, using a fluorescence microscope (CKX41, available from Olympus Corporation).

A: Successful adhesion of the cells to the cell adhesive portions in the pattern was observed.

B: Successful adhesion of the cells to the cell adhesive portions in the pattern was not observed.

[Cell Pattern Shape Accuracy (Evaluation of Pattern Resolution)]

The cell pattern shape accuracy was evaluated according to the criteria described below, using a fluorescence microscope (CKX41, available from Olympus Corporation).

A: The cell pattern was successfully formed at a pitch of 300 micrometers.

B: The cell pattern was formed at a pitch greater than 300 micrometers.

[Probability at which Predetermined Number of Cells can be Located at Predetermined Cell Adhesive Portions (Evaluation of Cell Number Control)]

The number of cells located per cell adhesive portion dot having a diameter ($\phi$) of 100 micrometers was calculated based on a fluorescence image, and evaluated according to the criteria described below.

The dots used for evaluation were all of the total of forty dots, namely twenty dots and another twenty dots onto which liquid droplets were dropped, intending to locate six cells and ten cells, respectively.

A: The number of cells per dot was within ±20% of the intended number at more than or equal to 80% of the dots.

B: The number of cells per dot was within ±20% of the intended number at less than 80% of the dots.

[Probability at which Number of Cells Located was Desired Number (Evaluation of Cell Density)]

The number of cells located per cell adhesive portion dot having a diameter ($\phi$) of 100 micrometers was calculated based on a fluorescence image, and evaluated according to the criteria described below.

The dots used for evaluation were the twenty dots onto which liquid droplets were dropped, intending to locate ten cells.

A: The number of cells per clot was eight or more at more than or equal to 80% of the dots.

B: The number of cells per clot was eight or more at less than 80% of the dots.

[Survival Rate of Located Cells after Predetermined Time had Passed (Evaluation of Survival Rate of Cells)]

A stock solution obtained by dissolving propidium iodide as a dead cell nuclear stain (CELLSTAIN-PI, available from Dojindo Laboratories) in distilled water at 1 mg/mL was added at 10 microliters/5 mL onto the cell pattern having been left to stand still for 10 minutes. Subsequently, the resultant was cultured in an incubator for 10 minutes. Then, the ratio of dead cells present per dot was calculated using a fluorescence microscope and evaluated according to the criteria described below.

The dots used for evaluation were the twenty dots onto which liquid droplets were dropped, intending to locate ten cells.

A: The average survival rate of cells per dot was 75% or higher.

B: The average survival rate of cells per dot was lower than 75%.

Example 2

A cell tissue over which a cell pattern was formed was produced in the same manner as in Example 1, except that the cell drying inhibitor was changed to sodium alginate (0.1% by mass), and evaluated in the same manners as in Example 1.

The evaluation results of Example 2 are presented in Table 1.

Example 3

A cell tissue over which a cell pattern was formed was produced in the same manner as in Example 1, except that the cell drying inhibitor and the substrate having a non-adhesive surface were changed to the followings, and evaluated in the same manners as in Example 1.

The cell drying inhibitor was changed to collagen (CELL-MATRIX TYPE 1-A, available from Nitta Gelatin Inc.) (mass ratio of 0.05% by mass), and the substrate having a non-adhesive surface was changed to dimethyl polysiloxane (SYLGARD 184, available from Dow Corning Toray Co., Ltd., hereinafter referred to as PDMS).

PDMS was obtained by mixing a material for a base substrate and a curing agent at a mass ratio of 10:1, deaerating the mixture, and heating the resultant at 70 degrees C. for 2 hours.

The evaluation results of Example 3 are presented in Table 1.

Example 4

A cell tissue over which a cell pattern was formed was produced in the same manner as in Example 3, except that the cell adhesive material was changed to collagen, and evaluated in the same manners as in Example 1.

The evaluation results of Example 4 are presented in Table 1.

Example 5

A cell tissue over which a cell pattern was formed was produced in the same manner as in Example 3, except that the cell adhesive material was changed to fibrin, and evaluated in the same manners as in Example 1.

The fibrin used was obtained by mixing fibrinogen (Fibrinogen from bovine plasma F8630, available from SIGMA-ALDRICH Co., LLC.) (mass ratio of 0.2% by mass) with thrombin (Thrombin from bovine plasma T4648, available from SIGMA-ALDRICH Co., LLC.) (mass ratio of 0.2% by mass), and leaving the mixture to stand still at room temperature overnight.

The evaluation results of Example 5 are presented in Table 1.

Example 6

A cell tissue over which a cell pattern was formed was produced in the same manner as in Example 3, except that the cell adhesive material was changed to RGD peptide (for biochemical use, available from Wako Pure Chemical Industries Ltd.) (0.1% by mass), and evaluated in the same manners as in Example 1.

The evaluation results of Example 6 are presented in Table 1.

Example 7

A cell tissue over which a cell pattern was formed was produced in the same manner as in Example 3, except that the cell adhesive material was changed to gelatin particles (mass ratio of 2% by mass), and evaluated in the same manners as in Example 1.

The gelatin particles were produced according to the method described in the —Method for producing particles having cell adhesiveness— section described above, using gelatin (APH-250, available from Nitta Gelatin Inc.).

The evaluation results of Example 7 are presented in Table 1.

Example 8

A cell ink 1 in which NIH/3T3 was dispersed and a cell ink 2 in which a normal human dermal fibroblast (CC-2509, available from Lonza Japan Ltd., hereinafter referred to as NHDF) was dispersed were prepared. These cell inks were alternately located over the cell adhesive portions in the pattern.

The cell ink 2 was prepared in the same manner as preparing the cell ink 1, except that the cells were changed to NHDF and the dye was changed to a red fluorescent dye (CELL TRACKER RED, available from Life Technologies Corporation). In Example 8, a cell tissue over which a cell pattern was formed was produced in the same manner as in Example 1, except that the cell ink used was changed to "the cell ink 1" and "the cell ink 2". "The cell ink 1" or "the cell ink 2" was located per cell adhesive portion in the pattern, and different cell inks were located over adjoining cell adhesive portions.

Evaluation for a plurality of cells described below was also performed in addition to the same evaluations as in Example 1.

[Location of Plurality of Cells]

The cell pattern shape accuracy was evaluated according to the criteria described below, using a fluorescence microscope (CKX41, available from Olympus Corporation).

A: A cell pattern in which NIH/3T3 and NHDF were located alternately was successfully formed at a pitch of 300 micrometers or less.

B: A cell pattern in which NIH/3T3 and NHDF were located alternately was formed at a pitch greater than 300 micrometers.

The evaluation results of Example 8 are presented in Table 2.

Example 9

A cell tissue over which a cell pattern was formed was produced in the same manner as in Example 8, except that an inkjet method was used as a method for forming the cell adhesive portions in the pattern, and evaluated in the same manners as in Example 8.

<Formation of Cell Adhesive Portions in Pattern>
—Preparation of Cell Adhesive Material Ink—

As a cell adhesive material, fibronectin was dissolved in distilled water at a mass ratio of 0.05% by mass, to prepare a cell adhesive material ink.

—Step of Forming Cell Adhesive Portions in Pattern by Inkjet—

The cell adhesive material ink was filled in the liquid chamber of the cell adhesive material discharging head of the producing apparatus of FIG. 3D, discharged onto a PDMS base material to form dots having a diameter ($\phi$) of 100 micrometers at a pitch of 300 micrometers, and then dried, to form cell adhesive portions in the pattern over the substrate having a cell non-adhesive surface.

The evaluation results of Example 9 are presented in Table 2.

Example 10

—Contact Printing Method—

A cell tissue over which a cell pattern was formed was produced in the same manner as in Example 1, except that the contact printing method illustrated in FIG. 6A to FIG. 6F was used as a method for forming the cell adhesive portions in the pattern, matrigel (MATRIGEL GFR REF 354230, available from Corning Inc.) was used as a cell adhesive material, and a PDMS base material was used as the base material, and evaluated in the same manners as in Example 1.

<Formation of Cell Adhesive Portions in Pattern>
—Preparation of Cell Adhesive Material Ink—

As a cell adhesive material, matrigel was dissolved in distilled water at a mass ratio of 0.05% by mass, to prepare a cell adhesive material ink.

—Step of Forming Cell Adhesive Portions in Pattern by Contact Printing—

The cell adhesive material ink was coated over a PDMS plate over which posts having a diameter ($\phi$) of 100 micrometers and a height of 50 micrometers were formed, to transfer the cell adhesive material ink onto a substrate (PDMS) having a cell non-adhesive surface, to form cell adhesive portions.

The evaluation results of Example 10 are presented in Table 3.

Example 11

—Formation of Cell Non-Adhesive Pattern with Poly-HEMA (Negative Printing, Mask Step) —

A cell tissue over which a cell pattern was formed over a cell adhesive substrate was produced by forming a cell non-adhesive pattern in the same manner as in Example 1, except that the method illustrated in FIG. 7A to FIG. 7F was used as a method for forming cell non-adhesive portions in the pattern, poly-HEMA (Poly(2-hydroxyethyl methacrylate), available from SIGMA-ALDRICH Co., LLC.) was used as a cell non-adhesive material, and a 60 mm dish (IWAKI TISSUE CULTURE DISH CODE 3010-060, available from AGC Techno Glass Co., Ltd.) was used as the cell adhesive substrate, and evaluated in the same manners as in Example 1.

<Formation of Cell Adhesive Portions in Pattern>
—Preparation of Cell Non-Adhesive Material Ink—

As a cell non-adhesive material, poly-HEMA (50 microliters) was dissolved in ethanol (ETHANOL (99.5), available from Wako Pure Chemical Industries Ltd.) (1 mL), to prepare a cell non-adhesive material ink.

The evaluation results of Example 11 are presented in Table 3.

Example 12

—Formation of cell non-adhesive pattern with alginic acid (negative printing, IJ step)—

A cell tissue over which a cell pattern was formed over a cell adhesive substrate was produced by forming a cell non-adhesive pattern in the same manner as in Example 11, except that the method illustrated in FIG. 8A to FIG. 8D was used as a method for forming cell non-adhesive portions in the pattern, and the same calcium alginate gel as described above was used as a cell non-adhesive material, and evaluated in the same manners as in Example 1.

<Formation of Cell Adhesive Portions in Pattern>
—Preparation of Cell Non-Adhesive Material Ink—

A sodium alginate solution obtained by dissolving sodium alginate (SKAT ONE, available from Kimica Corporation) in distilled water at a mass ratio of 2% by mass, and a calcium chloride solution obtained by dissolving calcium chloride dehydrate (available from Wako Pure Chemical Industries Ltd.) in distilled water at 100 mmol/L were prepared as cell non-adhesive materials.

—Step of Forming Cell Non-Adhesive Portions in Pattern by Inkjet—

The sodium alginate solution and the calcium chloride solution were discharged by inkjet onto the cell adhesive substrate, to cause the solutions to undergo gelation in a mixed state over the substrate, to form the cell non-adhesive pattern over the cell adhesive substrate.

The evaluation results of Example 12 are presented in Table 3.

Example 13

—Formation of Cell Non-Adhesive Pattern with Poly-HEMA (Negative Printing, Contact Printing)—

A cell tissue over which a cell pattern was formed over a cell adhesive substrate was produced by forming a cell non-adhesive pattern in the same manner as in Example 11, except that the contact printing method illustrated in FIG. 9A to FIG. 9F was used as a method for forming cell non-adhesive portions in the pattern, and evaluated in the same manners as in Example 1.

The evaluation results of Example 13 are presented in Table 3.

Example 14

—Formation of Cell Non-Adhesive Pattern with Collagen+PDMS (Negative Printing, IJ Step)—

A cell tissue over which a cell pattern was formed over a cell adhesive substrate was produced by forming a cell adhesive pattern in the same manner as in Example 1 and Example 11, except that the method illustrated in FIG. 10A to FIG. 10D was used as a method for forming a cell adhesive pattern and a cell non-adhesive pattern over the substrate, a glass slide (S1111, available from Matsunami Glass Ind., Ltd.) was used as the cell adhesive substrate, collagen was used as a cell adhesive material, and PDMS was used as a cell non-adhesive material, and evaluated in the same manners as in Example 1.

<Formation of Cell Adhesive Portions in Pattern>

The cell non-adhesive material was coated over the mask film used in Example 1, and the mask film was peeled subsequently, to form a cell non-adhesive pattern.

Collagen was discharged by inkjet in the same manner as in Example 9 to positions at which the non-adhesive pattern was absent, to form a cell adhesive pattern.

The evaluation results of Example 14 are presented in Table 3.

Comparative Example 1

A cell tissue was produced in the same manner as in Example 8, except that fibronectin was used as the cell adhesive material, and the cell adhesive material was coated without being passed through a mask pattern (i.e., resulting in no cell adhesive portions in the pattern being formed), and evaluated in the same manners as in Example 8.

The evaluation results of Comparative Example 1 are presented in Table 2.

Comparative Example 2

A cell tissue was produced in the same manner as in Example 8, except that a cell drying inhibitor was not added in the cell ink, and evaluated in the same manners as in Example 8.

The evaluation results of Comparative Example 2 are presented in Table 2.

Comparative Example 3

A cell tissue was produced in the same manner as in Example 9, except that cell suspensions of NIH/3T3 and NHDF were prepared respectively without adding a cell drying inhibitor, and the cell suspensions were seeded manually by $5 \times 10^4$ cells/mL per cell suspension and $1 \times 10^5$ cells/mL in total, and evaluated in the same manners as in Example 8.

The evaluation results of Comparative Example 3 are presented in Table 2.

TABLE 1

|  | Ex. 1 | Ex. 2 | Ex. 3 | Ex. 4 | Ex. 5 | Ex. 6 | Ex. 7 |
|---|---|---|---|---|---|---|---|
| Initial adhesion time | A | A | A | A | A | A | A |
| Resolution | A | A | A | A | A | A | A |
| Cell number control | A | A | A | A | A | A | A |
| Cell density | A | A | A | A | A | A | A |
| Cell survival | A | A | A | A | A | A | A |

TABLE 2

|  | Ex. 8 | Ex. 9 | Comp. Ex. 1 | Comp. Ex. 2 | Comp. Ex. 3 |
|---|---|---|---|---|---|
| Initial adhesion time | A | A | A | B | B |
| Resolution | A | A | B | B | B |
| Cell number control | A | A | A | A | B |
| Cell density | A | A | B | B | A |
| Cell survival | A | A | A | B | A |
| Plurality of cells | A | A | B | B | B |

TABLE 3

|  | Ex. 10 | Ex. 11 | Ex. 12 | Ex. 13 | Ex. 14 |
|---|---|---|---|---|---|
| Initial adhesion time | A | A | A | A | A |
| Resolution | A | A | A | A | A |

TABLE 3-continued

|  | Ex. 10 | Ex. 11 | Ex. 12 | Ex. 13 | Ex. 14 |
|---|---|---|---|---|---|
| Cell number control | A | A | A | A | A |
| Cell density | A | A | A | A | A |
| Cell survival | A | A | A | A | A |

As regards the results of Comparative Example 1, it was impossible to control the positions at which the cells would adhere when the cells landed, because no cell adhesive portions in the pattern were formed. Hence, not only was it impossible to form a cell pattern at the intended pitch but also the cell density was low in the region with the set diameter ($\phi$) of 100 micrometers.

As regards the results of Comparative Example 2, the survival rate of the cells was low because a cell drying inhibitor was not added in the cell ink. The dead cells also failed in adhering to the substrate.

As regards the results of Comparative Example 3, the cells adhered to all over the substrate and the pattern shape accuracy of the cell pattern was poor, because the cells were not located by liquid droplet discharging by inkjet. The cells over regions having a weak cell adhesiveness were peeled through washing of gently flowing serum-free D-MEM, to result in that the cells adhered along cell adhesive portions in the pattern. However, NIH/3T3 and NHDF each randomly adhered. Hence, it was impossible to locate two kinds of cells in an optional manner. Further, there were some positions from which the cell adhesive portions in the pattern were peeled due to the washing.

The present disclosure can provide a cell tissue producing method that would exhibit favorable results in all of the survival rate of cells, the cell pattern resolution, the cell density, and the cell number control, which are the factors of significance in the formation of a cell pattern. Moreover, the present disclosure makes it possible to form a cell pattern in which two or more kinds of cells are located in an optional manner.

Aspects of the present disclosure are, for example, as follows.

<1> A cell tissue producing method including:
forming a cell adhesive portion formed of a cell adhesive material and having a predetermined shape at a predetermined position over a substrate having a cell non-adhesive surface; and
discharging a cell suspension containing at least cells and a cell drying inhibitor onto the cell adhesive portion in the form of a liquid droplet to locate the cells.

<2> The cell tissue producing method according to <1>, wherein the forming the cell adhesive portion is performed by discharging a solution containing the cell adhesive material in the form of a liquid droplet to locate the liquid droplet over the substrate having the cell non-adhesive surface.

<3> The cell tissue producing method according to <1> or <2>,
wherein the cell drying inhibitor contains at least any one selected from the group consisting of polyvalent alcohols, gelatinous polysaccharides, and proteins selected from an extracellular matrix.

<4> The cell tissue producing method according to any one of <1> to <3>,
wherein the cell adhesive material contains a protein formed of an extracellular matrix.

<5> A cell tissue producing apparatus including:
a cell adhesive portion forming unit configured to form a cell adhesive portion formed of a cell adhesive material and having a predetermined shape at a predetermined position over a substrate having a cell non-adhesive surface; and
a cell locating unit configured to discharge a cell suspension containing at least cells and a cell drying inhibitor onto the cell adhesive portion in the form of a liquid droplet to locate the cells.

<6> A non-transitory recording medium storing a cell tissue producing program causing a computer to execute a process including:
forming a cell adhesive portion formed of a cell adhesive material and having a predetermined shape at a predetermined position over a substrate having a cell non-adhesive surface; and
discharging a cell suspension containing at least cells and a cell drying inhibitor onto the cell adhesive portion in the form of a liquid droplet to locate the cells.

<7> A cell tissue producing method including:
forming a cell non-adhesive portion formed of a cell non-adhesive material and having a predetermined shape at a predetermined position over a substrate having a cell adhesive surface, to form a cell adhesive portion, which is an exposed portion of the cell adhesive surface; and
discharging a cell suspension containing at least cells and a cell drying inhibitor onto the cell adhesive portion in the form of a liquid droplet to locate the cells.

<8> The cell tissue producing method according to <7>, wherein the forming the cell adhesive portion is performed by discharging a solution containing the cell non-adhesive material in the form of a liquid droplet to locate the liquid droplet over the substrate having the cell adhesive surface.

<9> The cell tissue producing method according to <7> or <8>,
wherein the forming the cell adhesive portion is performed by discharging a solution containing a cell adhesive material in the form of a liquid droplet onto the substrate over which the cell non-adhesive portion is formed, to locate the liquid droplet over the substrate free of the cell non-adhesive portion to form the cell adhesive portion formed of the cell adhesive material.

<10> A cell tissue producing apparatus including:
a cell adhesive portion forming unit configured to form a cell non-adhesive portion formed of a cell non-adhesive material and having a predetermined shape at a predetermined position over a substrate having a cell adhesive surface, to form a cell adhesive portion, which is an exposed portion of the cell adhesive surface; and
a cell locating unit configured to discharge a cell suspension containing at least cells and a cell drying inhibitor onto the cell adhesive portion in the form of a liquid droplet to locate the cells.

<11> A non-transitory recording medium storing a cell tissue producing program causing a computer to execute a process including:
forming a cell non-adhesive portion formed of a cell non-adhesive material and having a predetermined shape at a predetermined position over a substrate having a cell adhesive surface, to form a cell adhesive portion, which is an exposed portion of the cell adhesive surface; and
discharging a cell suspension containing at least cells and a cell drying inhibitor onto the cell adhesive portion in the form of a liquid droplet to locate the cells.

The cell tissue producing method according to any one of <1> to <4> and <7> to <9>, the cell tissue producing apparatus according to <5> or <10>, and the non-transitory recording medium storing a cell tissue producing program according to <6> or <11> can solve the various problems in the related art and can achieve the object of the present disclosure.

What is claimed is:

1. A cell tissue producing method, comprising:
forming a cell adhesive portion formed of a cell adhesive material and having a predetermined shape at a predetermined position over a substrate having a cell non-adhesive surface; wherein the cell adhesive material consists of at least one material selected from the group consisting of an extracellular matrix protein, gelatin, and water; wherein the cell adhesive material is cross-linked; and wherein the cell adhesive portion is formed on the substrate by at least one process selected from the group consisting of a, b, and c:
a) drawing a pattern on the substrate with a film or weakly adhesive tape to form a mask film;
coating the adhesive material on the film or weakly adhesive tape;
drying the adhesive material; and
removing the mask film;
b) discharging droplets of the cell adhesive material on to the substrate in the predetermined shape and at the predetermined position; or
c) coating the cell adhesive material on a printing plate; and
transferring the cell adhesive material to the substrate; and
discharging a cell suspension onto the cell adhesive portion in a form of a liquid droplet to locate the cells, wherein the cell suspension comprises cells and a polyvalent alcohol or gelatinous polysaccharide.

2. The cell tissue producing method according to claim 1, wherein the forming the cell adhesive portion is performed by discharging droplets of the cell adhesive material.

3. The cell tissue producing method according to claim 1, wherein an extracellular matrix protein is included in the cell adhesive material.

4. The cell tissue producing method according to claim 1, wherein the cell adhesive portion is formed on the substrate by drawing a pattern on the substrate with a film or weakly adhesive tape to form a mask film; coating the adhesive material on the film or weakly adhesive tape; drying the adhesive material; and removing the mask film.

5. The cell tissue producing method according to claim 1, wherein the cell adhesive portion is formed on the substrate by coating the cell adhesive material on a printing plate and transferring the cell adhesive material to the substrate.

6. A cell tissue producing method, comprising:
forming a cell non-adhesive portion formed of a cell non-adhesive material and having a predetermined shape at a predetermined position over a substrate having a cell adhesive surface, to form a cell adhesive portion, which is an exposed portion of the cell adhesive surface; wherein the cell non-adhesive material consists of at least one material selected from the group consisting of polydimethyl siloxane (PDMS), a metal alginate, a polyhydroxyethyl methacrylate (pHEMA), a polyethylene glycol (PEG), and water; and wherein the cell non-adhesive portion is formed on the substrate by at least one process selected from the group consisting of a and b:
a) discharging droplets of the cell non-adhesive material on to the substrate in the predetermined shape and at the predetermined position; or
b) coating the cell non-adhesive material on a printing plate; and
transferring the cell non-adhesive material to the substrate; and
discharging a cell suspension onto the cell adhesive portion in a form of a liquid droplet to locate the cells, wherein the cell suspension comprises cells and a polyvalent alcohol or gelatinous polysaccharide.

7. The cell tissue producing method according to claim 6, wherein the forming the cell adhesive portion is performed by discharging droplets of the cell non-adhesive material.

8. The cell tissue producing method according to claim 6, wherein the forming the cell adhesive portion is performed by discharging a solution that comprises a cell adhesive material in a form of a liquid droplet onto the substrate over which the cell non-adhesive portion is formed, to locate the liquid droplet over the substrate free of the cell non-adhesive portion to form the cell adhesive portion formed of the cell adhesive material.

9. The cell tissue producing method according to claim 6, wherein the cell non-adhesive portion is formed on the substrate by coating the cell non-adhesive material on a printing plate and transferring the cell non-adhesive material to the substrate.

* * * * *